United States Patent [19]
Feygin et al.

[11] Patent Number: 5,637,175
[45] Date of Patent: Jun. 10, 1997

[54] APPARATUS FOR FORMING AN INTEGRAL OBJECT FROM LAMINATIONS

[75] Inventors: Michael Feygin, Rancho Palos Verdes; Sung S. Pak, Chula Vista, both of Calif.

[73] Assignee: Helisys Corporation, Torrance, Calif.

[21] Appl. No.: 319,980

[22] Filed: Oct. 7, 1994

Related U.S. Application Data

[63] Continuation-in-part of Ser. No. 671,720, Apr. 4, 1991, Pat. No. 5,354,414, continuation of PCT/US89/04357, Oct. 4, 1989, which is a continuation of Ser. No. 253,845, Oct. 5, 1988, abandoned.

[51] Int. Cl.$^6$ ..................................................... B32B 31/00
[52] U.S. Cl. ........................... 156/264; 156/256; 156/267; 156/272.8; 156/275.5; 156/329.8; 156/329.9; 156/512; 156/538; 264/405; 425/124.4
[58] Field of Search ........................... 156/58, 59, 62.2, 156/250, 256, 264, 265, 272.2, 272.8, 353, 379.6, 379.8, 379.9, 380.9, 510, 512, 267, 275.5, 538; 264/405; 425/174.2

[56] References Cited

U.S. PATENT DOCUMENTS

| | | | |
|---|---|---|---|
| 702,615 | 6/1902 | Barden | 273/157 R |
| 1,524,972 | 2/1925 | Hampson | 434/96 |
| 2,138,024 | 11/1938 | Cheesman | 434/150 |
| 2,242,631 | 5/1941 | Stillman | 156/59 |
| 2,556,798 | 6/1951 | Conrcordet | 434/152 |
| 3,137,080 | 6/1964 | Zang | 434/152 |
| 3,280,230 | 10/1966 | Bradshaw, Jr. et al. | 264/448 |
| 3,301,725 | 1/1967 | Frontera | 156/59 |
| 3,534,396 | 10/1970 | Hart, et al. | 364/474.24 |
| 3,539,410 | 11/1970 | Meyer | 156/58 |
| 3,551,270 | 12/1970 | Sharkey | 428/138 |
| 3,589,507 | 6/1971 | Greenberg | 206/575 |
| 3,932,923 | 1/1976 | DiMatteo | 29/407 |
| 4,041,476 | 8/1977 | Swainson | 340/173 CC |
| 4,078,229 | 3/1978 | Swanson et al. | 340/173 CM |
| 4,196,737 | 4/1980 | Bevilacqua | 128/798 |
| 4,238,840 | 12/1980 | Swainson | 365/119 |
| 4,288,861 | 9/1981 | Swainson et al. | 365/127 |
| 4,323,756 | 4/1982 | Brown et aL. | 219/121 LF |
| 4,361,262 | 11/1982 | Israeli | 228/118 |
| 4,393,450 | 7/1983 | Jerard | 364/474 |
| 4,323,756 | 4/1982 | | |

(List continued on next page.)

FOREIGN PATENT DOCUMENTS

| | | |
|---|---|---|
| 906643 | 8/1972 | Canada. |
| 2368101 | 6/1978 | France. |
| 2263777 | 7/1973 | Germany. |
| 2743544 | 3/1979 | Germany. |
| 60-102234 | 6/1985 | Japan. |
| 60-102236 | 6/1985 | Japan. |
| 23709 | of 1901 | United Kingdom. |
| 652969 | 5/1951 | United Kingdom. |
| 0938455 | 10/1963 | United Kingdom. |

OTHER PUBLICATIONS

Incropera, et al., "Fundamentals of Heat Transfer," John Wiley & Sons, NY 1981 p. 544.

Feygin, M., "Laser CIM in 3-D Complex Objects Production," *Industrial Laser Review* Jun. 1987.

(List continued on next page.)

*Primary Examiner*—James Sells
*Attorney, Agent, or Firm*—Knobbe, Martens, Olsons & Bear, LLP

[57] ABSTRACT

The present invention generally relates to manufacturing apparatus for forming an integral three-dimensional object from individually contoured laminations of the same or gradually varying shape, successive laminae of that object being produced out of thin sheet or powder based materials through the cutting, fusing or physicochemical property changing action generated by a computer directed beam of concentrated energy or matter, successive substantially planar laminations of that object being automatically stacked together for step-wise laminar buildup of the desired three-dimensional object.

35 Claims, 23 Drawing Sheets

U.S. PATENT DOCUMENTS

| | | | |
|---|---|---|---|
| 4,575,330 | 3/1986 | Hull | 425/174.4 |
| 4,665,492 | 5/1987 | Masters | 364/468 |
| 4,687,526 | 8/1987 | Wilfert | 156/64 |
| 4,752,352 | 6/1988 | Feygin | 156/630 |
| 4,752,498 | 6/1988 | Fudim | 427/54.1 |
| 4,801,477 | 1/1989 | Fudim | 427/54.1 |
| 4,814,296 | 3/1989 | Jedlicka et al. | 437/226 |
| 4,847,137 | 7/1989 | Kellen et al. | 428/195 |
| 4,863,538 | 9/1989 | Deckard | 156/62.2 |
| 4,880,486 | 11/1989 | Maeda | 156/273.5 |
| 4,945,203 | 7/1990 | Soodak et al. | 219/121.64 |
| 4,961,154 | 10/1990 | Pomerantz et al. | 364/522 |
| 5,002,854 | 3/1991 | Fan et al. | 430/270.1 |
| 5,015,312 | 5/1991 | Kinzie | 156/63 |
| 5,037,416 | 8/1991 | Allen et al. | 604/385.1 |
| 5,094,935 | 3/1992 | Vassiliou et al. | 264/401 |
| 5,174,843 | 12/1992 | Natter | 156/155 |

OTHER PUBLICATIONS

Kunieda, et al., "Manufacturing of Laminated Deep Drawing Dies by Laser Beam Cutting," Proceedings of the First International Conference on Technology of Plasticity *Advanced Technology of Plasticity* 1984, Val. pp. 520–525.

"Sculpting Parts With Light," *Machine Design* (Mar. 6, 1986).

Pomerantz, "Automated Modeling Machines," NCGA 1989 Conference Proceedings, Apr. 17–20, 1989 (Cubital).

"Desktop Mgg." published report, Technical Insights, Inc., 1988 (Desktop Mfg. Inc./University of Texas).

Nakagawa, T., "Laser cut sheet laminated forming dies by duffusion bonding," *Proceedings of the Twenty–FIGth International Machine Tool Design and Research Conference* Birmingham, 22nd–24th Apr. 1985, pp. 505–510.

Article of Dr. Takeo Nakagawa, in Magazine "NEC Factory Engineering", vol. 34, published: Jul. 20, 1984.

Article of M. Kunieda and Takeo Nakagawa. published in Bul. Japan Soc. of Prec. Engg. vol. 18, No. 4 (Dec. 1984), pp. 353, 354.

Takeo Nakagawa, M. Kunieda and Sheng–Dong Liu in Proc. of 25th International Machine Tool Design Research Conference, pp. 505to 510, published in 1984.

Takeo Nakagawa, International Forum 1985 on Die and Mold, New Developments in the Manufacturing of Die and Mold, pp. 209 to 218, published in 1985.

Retallick, D.A., Switching theory Applied to Fluidic digital Systems, University of Birmingham, Sep. 1968.

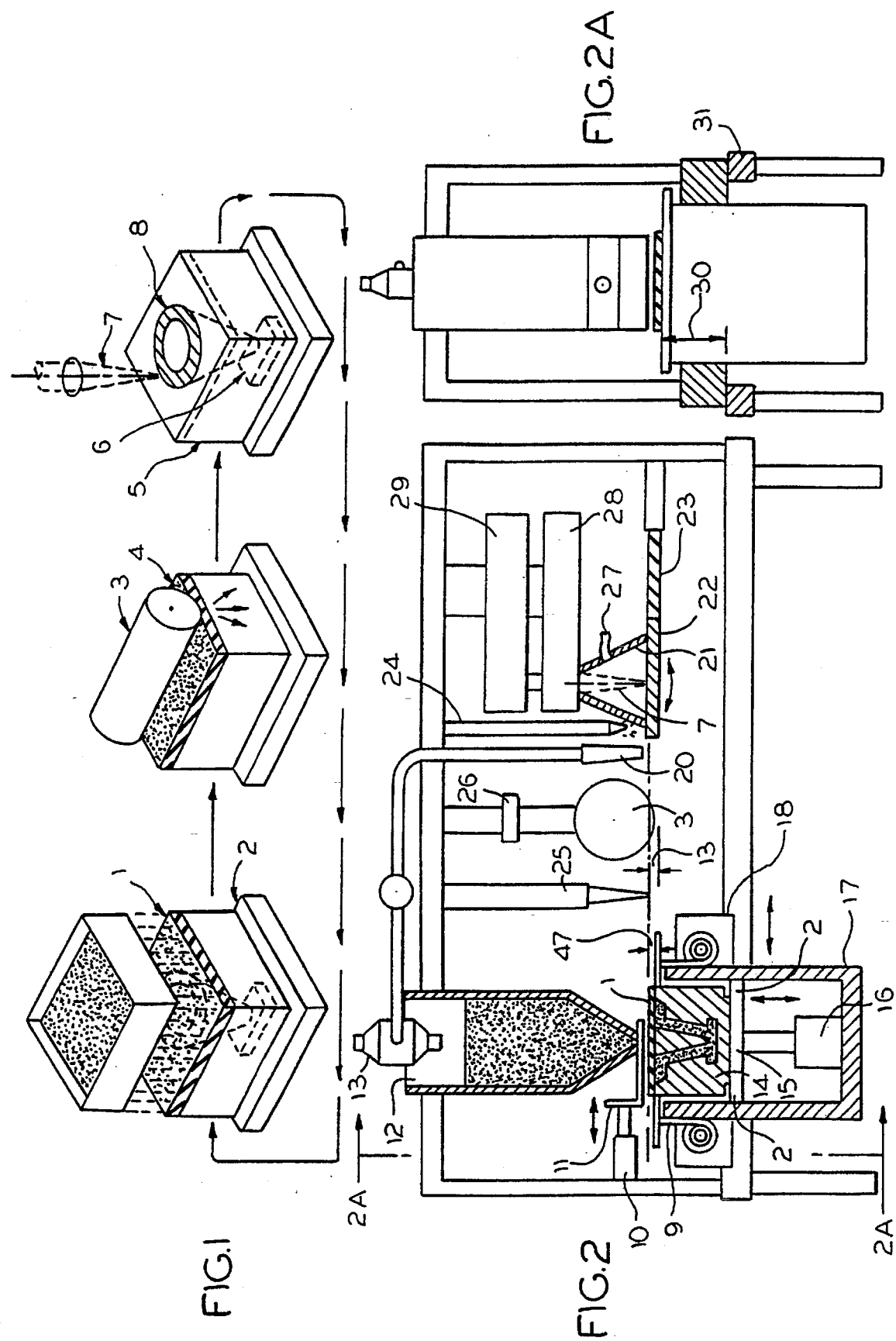

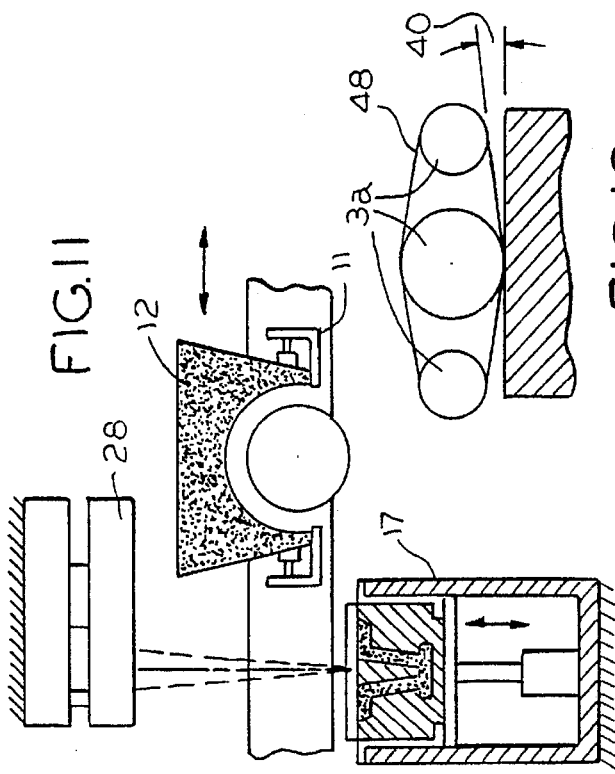
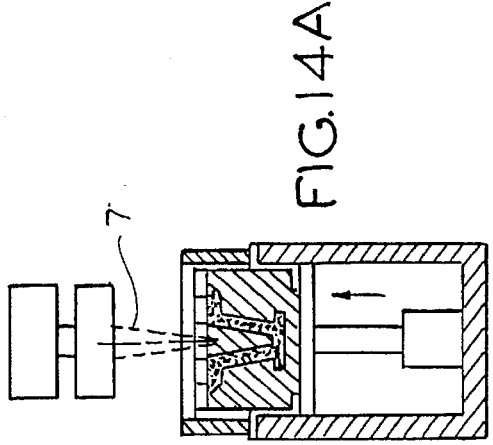
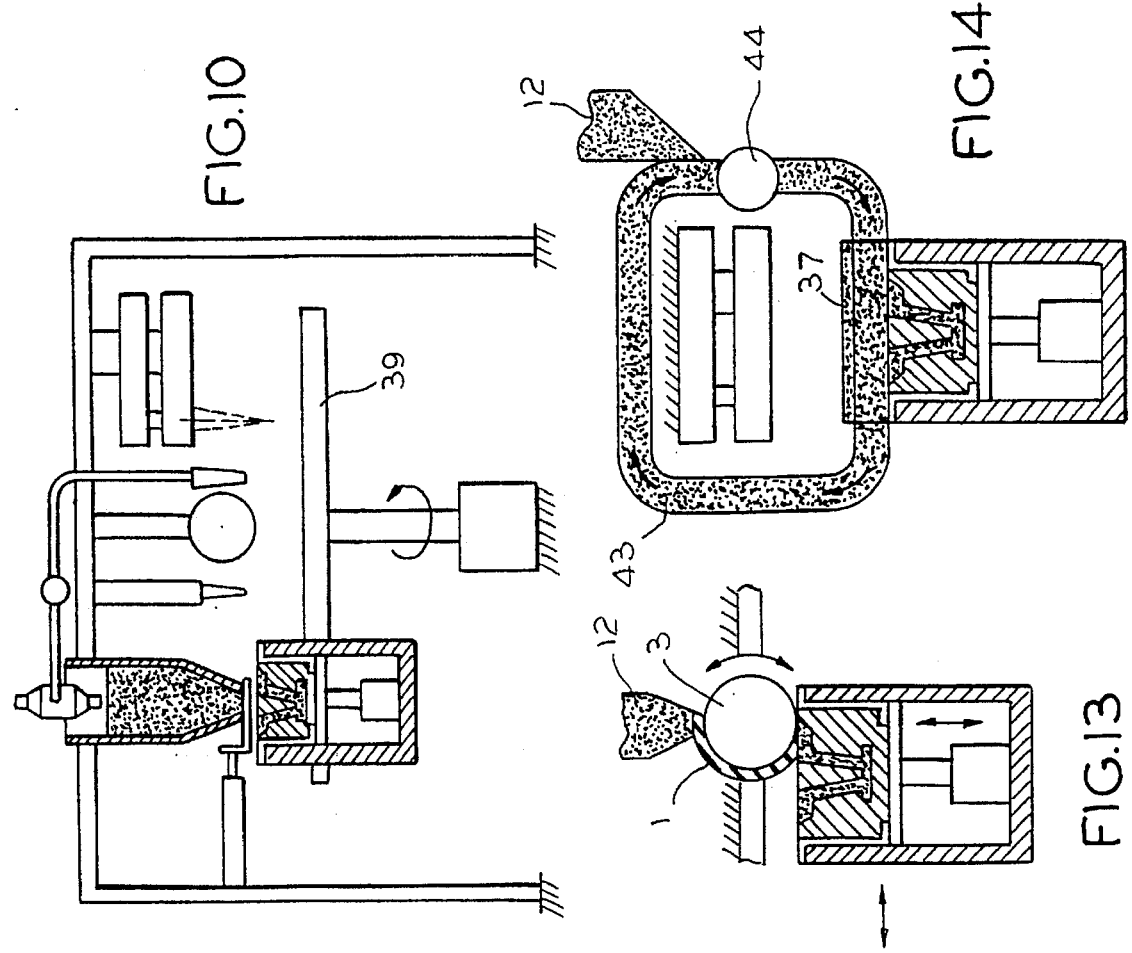

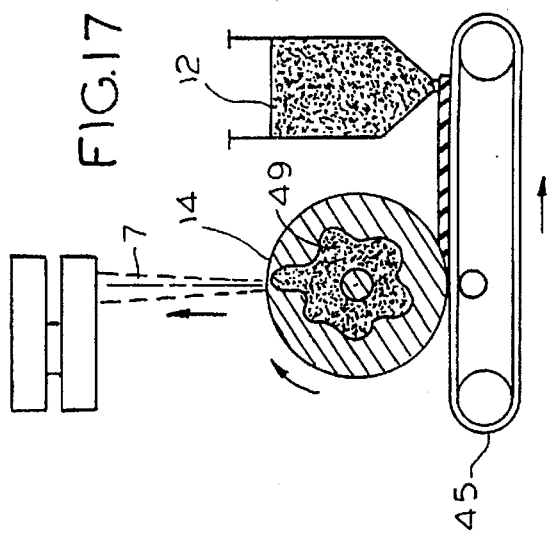
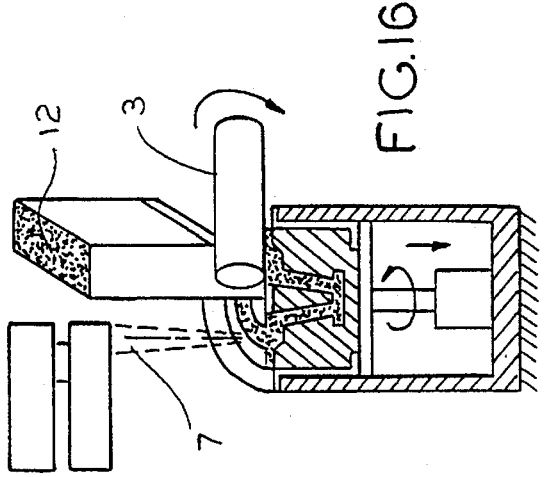
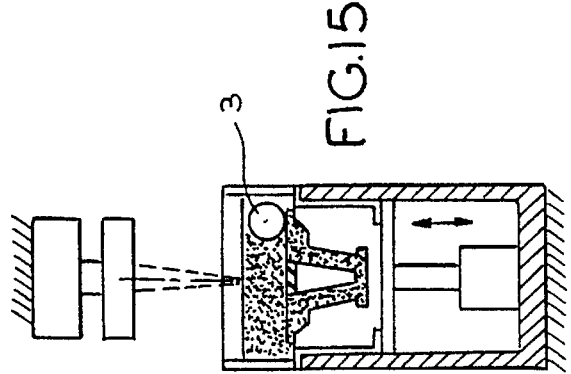
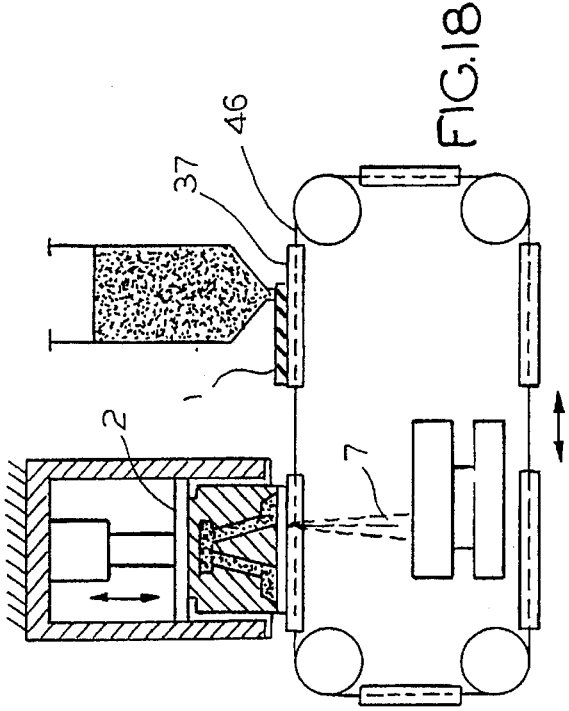
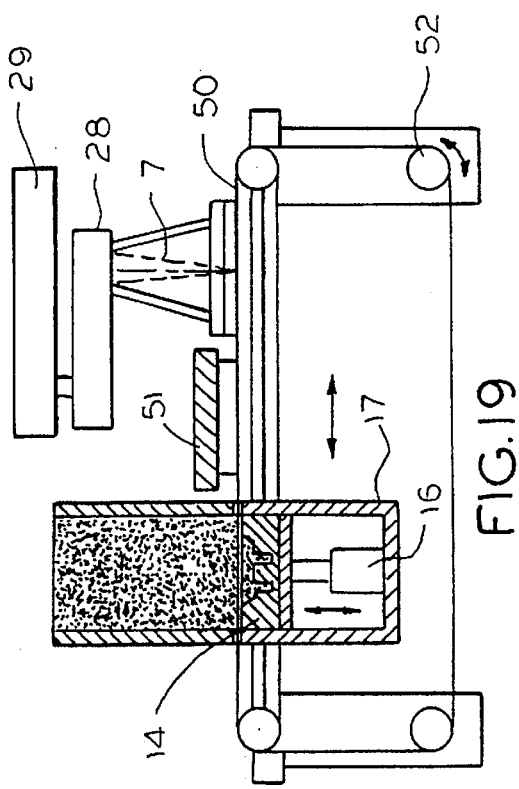

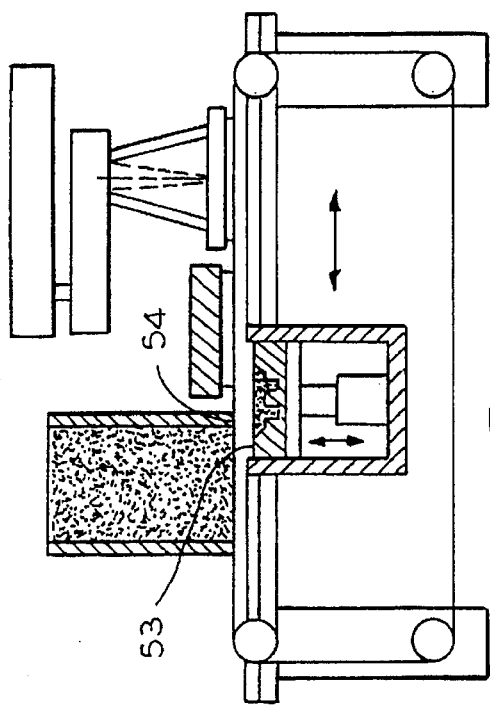
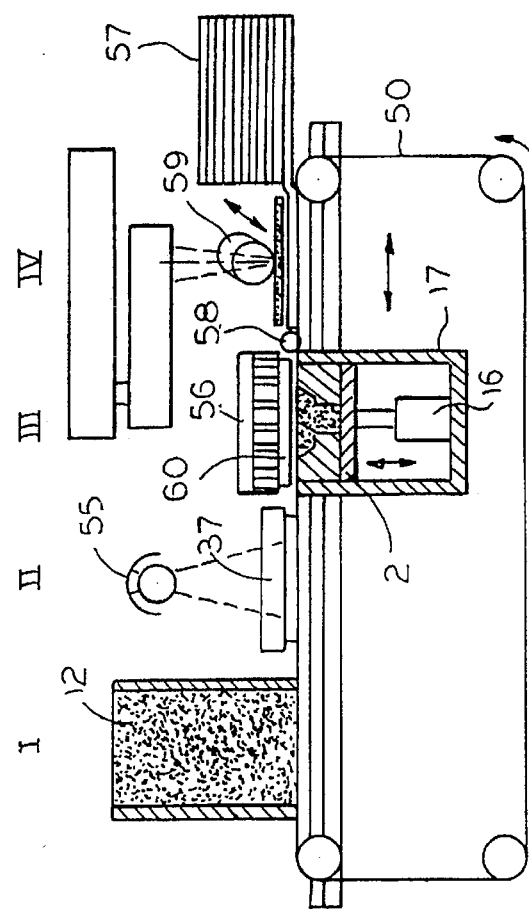
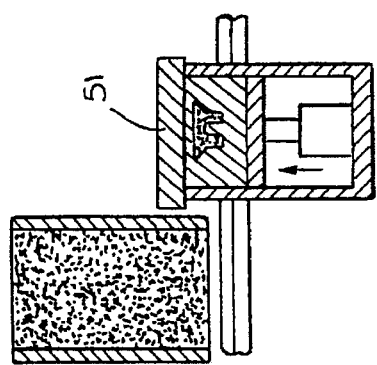
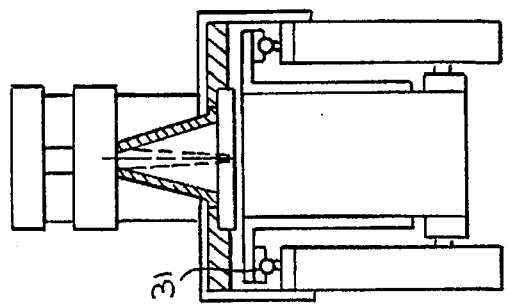
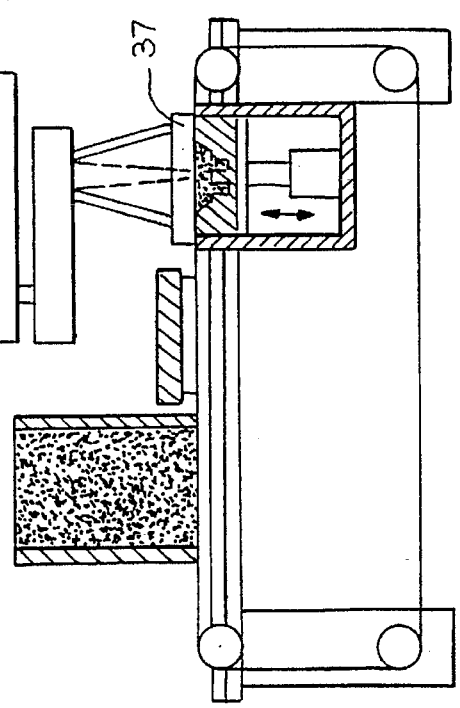
FIG.22
FIG.24
FIG.21
FIG.23
FIG.20

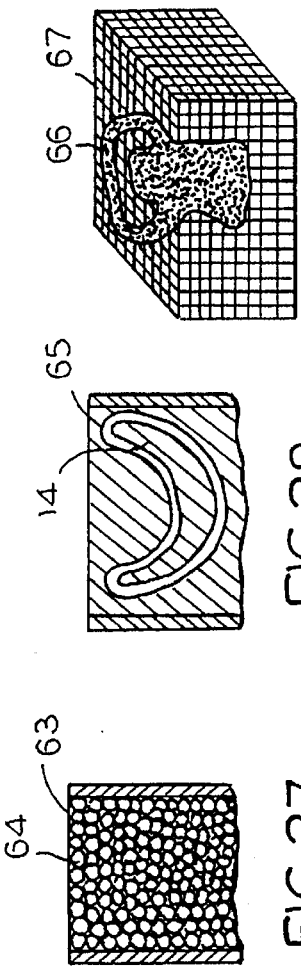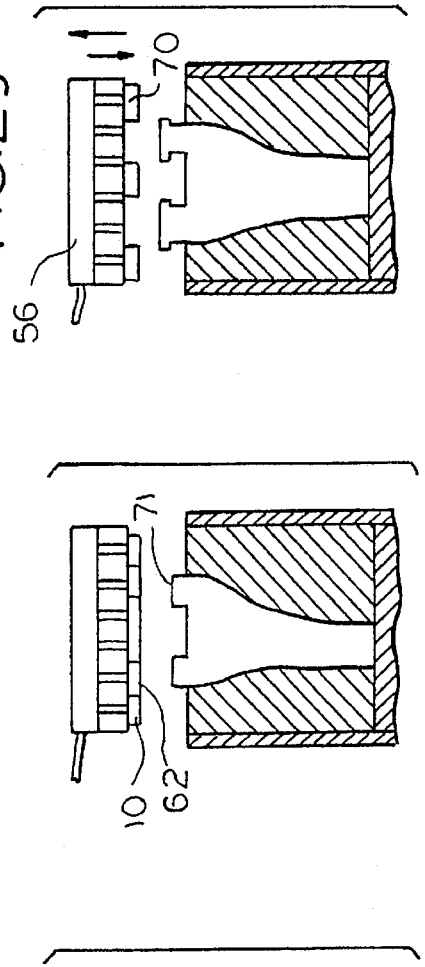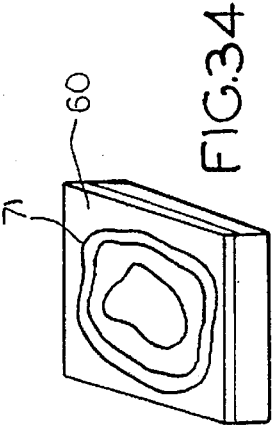

APPARATUS FOR FORMING AN INTEGRAL OBJECT FROM LAMINATIONS

This application is a continuation-in-part of U.S. patent application Ser. No. 07/671,720 filed Apr. 4, 1991, U.S. Pat. No. 5,354,414, which is a continuation of PCT application Ser. No. US89/04357, filed Oct. 4, 1989, which is a continuation-in-part of U.S. patent application Ser. No. 253,845 filed Oct. 5, 1988, now abandoned.

TECHNICAL FIELD

This invention relates to the improvements in laminated object manufacturing (LOM) method and apparatus for forming three-dimensional objects out of laminations, and more particularly to the techniques relying on laminations produced out of powder based or sheet materials. The laminated object manufacturing process aims at automated production of metal, plastic, ceramic, and composite parts of unlimited complexity directly from a computer generated image.

Background Art

In order to understand the advantages which LOM system offers one has to consider how small batches of parts are usually produced. In conventional manufacturing the part's design is first created using computer aided design (CAD) or other drafting techniques. Later, manufacturing operations are defined and the prototype is painstakingly produced by conventional cutting or forming processes, often requiring skilled labor, considerable time and expense. Multiple tools and machines are used in such production as a rule. After the prototype testing, design changes are likely to occur, and laborious production process has to be repeated until the design is optimized.

Therefore, the ability to manufacture prototypes or small batches of parts directly as a computer output utilizing a single production device is highly desirable. If the modification of the design is needed after the part has been examined, a necessary change can be done on the computer screen and another "hard" copy can be created by the LOM system.

In general, the family of LOM systems proposed herein use laser as a tool for forming laminations and bonding them into a stack. In recent years, flexibility and responsiveness of laser based systems motivated a number of organizations and inventors to apply them in the three-dimensional object production. Several techniques based on two intersecting laser beams selectively solidifying ultra violet (UV) curable liquids at the point of their intersection deep within the liquid medium have been described in U.S. Pat. Nos. 4,041,476, 4,078,229, 4,238,840 and 4,288,861. These systems have suffered from a number of problems related to their resolution, exposure control and difficulties related to synchronous control of two intersecting laser beams.

A more successful process and system has been proposed by Charles W. Hull in U.S. Pat. No. 4,575,330. The stereolithography process described in this patent generates three-dimensional objects by curing a UV curable material with a single laser beam focused on the surface of a platform placed in a vat of a UV curable plastic. As the beam cures a cross-section of the part the platform makes an incremental move down thus exposing another layer of liquid plastic. The beam scans the new surface within the pattern of the desired cross-section solidifying the plastic material within that pattern and attaching it to the previous cross-section. The step is repeated until the desired object is produced.

In spite of a number of advantages gained by this method with respect to earlier technologies the method has a disadvantage of being capable of producing parts out of liquid (mainly UV curable) polymers only. These polymers represent a relatively limited group of materials. They are often toxic. The parts produced through the UV curing process are usually only partially cured and therefore are dimensionally and structurally unstable as they are removed from the vat.

In order to prevent their sinking into the liquid, a substantial support structure has to be designed and built for cross-sections located above the platform and unattached to other cross-sections at a particular level. The process also creates internal stresses within the plastic part created as a result of a shrinkage caused by the UV curing process. These stresses cause warpage of unsupported or suddenly expanding cross-sections and therefore make it difficult to create certain geometries. Thick walled parts are difficult to create for the same reason. The speed of the process is also limited by the low powers of currently available UV lasers.

Other developments have taken place with the use of powder materials in building near net shape three-dimensional parts. U.S. Pat. No. 4,323,756 of C. Brown, E. Brienan and H. Kear describes a technique for building parts in a layered fashion using high power energy beams to melt substrate surface and added stock. In this technique powder is deposited onto a substrate by blowing a stream of it through a nozzle coaxial with a laser beam heating and melting it along with the substrate as soon as the powder reaches the surface of the substrate. In order to direct the new powder to the desired places of the laminated part either the part or the nozzle have to be moved in a controlled fashion. This method has an obvious disadvantage associated with the necessity to overcome inertia of moving mechanical components. Also, the ability to deposit material in a precise fashion to achieve high resolution in the final product is questionable in this technique, since in order to be deposited, the material has to go through a nozzle.

Early concepts related to use of sheet materials in the three-dimensional parts buildup have been explored by Japanese scientists (See: Masonory Kunieda and Takeo Nakagawa "Manufacturing of Laminated Deep Drawing Dies by Laser Beam Cutting", Advanced Technology of Plasticity, Vol. 4 (1984)). Although some methods for laser cutting laminae and joining them together have been described, this work has not suggested ways of using the laminating technique for building a computer driven device which would transfer three-dimensional computer images into physical parts in one automated step.

U.S. Pat. No. 4,752,352 by Feygin, has suggested a number of methods and systems for accomplishing this goal. The current application relates to significant improvements on the methods and apparatus described in the earlier patent. These apparatus create three-dimensional parts out of substantially planar cross-sections utilizing powder based or sheet materials. The methods overcome the material limitations of the stereolithographical technique by making it possible to use a wide range of powder materials (including metals) as well as many plastic, metal and composite sheet materials for the laminated manufacturing of three-dimensional objects. At the same time they allow to achieve much greater speed and finer resolution than the process disclosed in the Brown et al. U.S. Pat. No. 4,323,756 patent by avoiding the material deposition through a nozzle, thus, allowing the use of scanning techniques in the energy beam manipulation.

Another type of an automated modelling system based on liquid polymers is being developed by an Israeli company, Cubital (See: Itzhak Pomerantz, "Automated Modeling Machines", NCGA 1989 conference proceedings, Apr. 17-20, 1989). Their system manufactures models out of liquid polymers by a multistep process. The steps of the technique are: deposit a thin layer of a UV curable polymer; illuminate the polymer through a xerographically produced mask having geometry of a single cross-section; suction off the liquid material surrounding the cured cross section; fill the areas surrounding the cross-section with a water soluble UV polymer, water, or wax serving as support; cure the rest of the layer or freeze the water; grind the surface to establish a uniform layer; repeat the earlier steps until the part is complete; thaw the ice, or melt the wax surrounding the part or dissolve the water soluble polymer. The process is very complex but it resolves some geometry problems present in stereolithography. Since the process is based on liquid UV curable polymers it does not resolve material limitations and internal stress and shrinkage problems related to stereolithography.

Still another technique relying on illumination of liquid polymers through a mask is being developed by Efrem Fudim of Light Sculpturing Inc. based in Wisconsin. His U.S. Pat. Nos. 4,752,498 and 4,801,477 describe several techniques which are somewhat similar to the earlier described method being developed by Cubital. These methods usually involve illumination of a UV curable polymer with a UV light through plotter generated masks and a piece of flat material transparent to the UV radiation and remaining in contact with the liquid layer being cured. Although the method is simpler than the Cubital technique and is much more energy efficient than stereolithography it has certain limitations related to unsupported geometries. It also relies on UV curable liquid polymers and, therefore, is limited by the properties (shrinkage, warpage, fragility, strength) and relatively small number of these materials. Still another development similar to my powder based LOM process is taking place at the Desktop Manufacturing Inc. (formerly Nova, Inc.) associated with the University of Texas (Austin). A process called "Selective Laser Sintering" has been under development by this company (See "Desktop Manufacturing" report published by Technical Insights, Inc. in 1988). The technique involves sequential deposition of thin layers of metal or plastic powders and selectively sintering these powders with a scanning laser beam. Our work has included conducting an extensive experimental investigation of the powder and sheet LOM processes using a prototype system which Michael Feygin, a co-inventor of this application, built at John Deere, Inc. Although a significant part of the present patent is dedicated to improvements on the powder technique, our current view is that the sheet LOM process may be superior to the powder technique. The powder technique, with currently available powders, has a serious problem of heat generated internal stresses which distort laminated objects and limit the number of available geometries even when the object is heat stabilized and then gradually lowered in temperature. Structural properties of parts created out of powder have to date been greatly inferior to the ones created out of sheet.

One more computer automated manufacturing technology related to the presently described development is sometimes called "Ballistic Particle Manufacturing". This is a dot matrix printer like technique for creating 3-D parts (U.S. Pat. No. 4,665,492). In this method, particles of molten material are deposited in a controlled fashion to create a three-dimensional part. This method is expected to have some problems related to internal stress and low resolution.

It is presently believed that the sheet based LOM method is the best proprietary technology among the ones described earlier. The majority of the related technologies are based on one or another form of a UV curable technique. Only one other process is related to the fusion of powders with lasers. None of them is based on sheet materials. Advantages of the sheet LOM process as compared to the ones described earlier are as follows:

1) The main competitive advantage of the sheet LOM process is in its ability to make parts out of far more off-the-shelf materials than UV curing techniques. Our work has already resulted in the production of parts out of metal, plastic, and paper. The paper based parts have properties similar to plywood.

2) Internal stress is a very serious problem in the stereolithography, Selective Laser Sintering (SLS), and Cubital (Solid Ground Curing) processes. The sheet LOM process produces virtually no internal stress, especially if the temperature of the part is maintained during construction and then gradually lowered.

3) The sheet technique is much faster than stereolithography or the powder LOM processes. The reasons are as follows:
  a) Due to the high viscosity of UV liquids, it takes a considerable amount of time to form a layer (even with the newly introduced wiper blade leveling the liquid). Although the curing step is faster in the Cubital process than that of stereolithography, a considerable amount of time is required to perform other steps of this multi step technique. Deposition of a sheet in the LOM process can be virtually instantaneous.
  b) Because of the fact that during the execution of the sheet process the laser beam outlines the periphery of a cross-section instead of raster painting its complete area as is done in UV or powder processes, thick walls are produced just as fast as thin ones. The only factor that matters is the periphery of a cross-section. Therefore, extremely large parts with thick walls (even ones which would be difficult to mold or cast) can be produced by this technique.

4) Model production has been chosen as an initial market by many in the field, since UV curable parts created by the 3-D Systems stereolithography process or Cubital's "Solid Ground Curing" technique are rather fragile and can not serve as functional parts yet. By creating several metal and plywood objects our work on the LOM process has demonstrated a clear potential to produce functional parts such as dies, molds, and production parts directly. So far there has not been any proof that laser beam scanning is a good way of producing structurally strong materials (when a laser beam scans a UV or powder cross section it creates the material out of which it will be made). On the other hand the LOM technique just outlines the geometry of a cross section by cutting it around its periphery. This preserves the original properties of the sheet material which has been earlier created by an extrusion, cold or hot rolling, or plastic film production processes.

5) Because in the sheet LOM technique, a part can be produced having an absence of appreciable internal stresses and the unpredictable shrinkage of parts associated with such internal stresses, there is a potential of manufacturing objects with the XY direction tolerances significantly higher than with internal stress affected techniques.

6) Processes relying on manufacturing out of UV curing polymers have been subject to strict OSHA scrutiny since they involve potentially harmful substances. The majority of sheet materials used in LOM process are considered safe.

7) Although virtually no waste is generated in the UV curing technique, the liquid polymers used in it are extremely expensive. Most of the sheet materials are over an order of magnitude cheaper.

8) Due to being a one step process (not requiring post curing operations), and because of high speed of production and lack of internal stresses, the sheet LOM process can produce extremely large parts just as efficiently as tiny ones.

9) The only process besides LOM which is capable of automated creation of unsupported (cantilever) geometries of unrestricted complexity is the one being developed by Cubital. However, their process is significantly more complex than the sheet LOM technique.

DISCLOSURE OF INVENTION

In general terms, the present invention provides a new and improved method and apparatus for manufacturing a three-dimensional object from laminations formed in shapes required for assembly in a preselected sequence. The apparatus contains means for storing and supplying a material together with means for forming the material into a plurality of individually contoured laminations. The lamination forming means are comprised of a beam of concentrated energy or a jet of concentrated matter. It also includes computer based means for defining the geometry of the laminations and for controlling the operation of lamination forming means. It further includes means for assembling the plurality of individually contoured laminations into a three-dimensional object and for integrally bonding each of the individually contoured laminations. With the unique apparatus of the invention, the formation of an integral three-dimensional object from laminations of the same or gradually varying shape can be successfully accomplished.

The process starts when a computer image of an object is created using available Computer Aided Design techniques. Later, the image is sliced with the use of the computer at multiple cross-sections located at a predetermined distance from each other. These cross-sections normally are at the top surface of a slice, but the instantaneous slope of the object at points of the surface of the object can be used to adjust the edge of a slice, so that the constructed object is closer to net shape than if each lamination was only the shape of the spaced cross-sections. The slope may also be taken into account to bevel the edge of a lamination to produce objects closer to net shape.

In a presently preferred embodiment, by way of example and not necessarily by way of limitation, a supply station houses a powder based material container located at the material depositing station. The apparatus also includes a cyclically traveling carriage which in the preferred embodiment moves reciprocally. The carriage carries a vertical stage with a laminations carrying platform located on it. The piston-like platform which is surrounded by a cylinder-like enclosure makes incremental moves down as thin powder layers are deposited onto it from the powder container. After each new layer of the powder is deposited it may be compressed on the platform through an action of a roller or a press. At this stage the geometrical information about the cross-sections of a three-dimensional object being manufactured is transmitted from the computer, where it was defined through computer aided design means, to a laser scanner which scans the newly deposited layer of powder with a focused laser beam. The powder affected by the laser beam changes its physical or chemical properties. Most often this change results in sintering or melting of the powder and fusing the material within the boundaries of a cross-section as well as bonding it to the previous cross-section. The characteristics of the beam may be changed when scanning adjacent the edge of the cross-section to provide a bevel thereto so that the constructed object more closely follow the computer generated object. After all of the cross-sections have been created by the apparatus the change in powder property is utilized in separating the material which belongs to the object from the material which surrounds it. The means for accomplishing this separation can be either mechanical such as blow off, impact, vibration or sand blasting, or chemical such as solution in a chemical media which affects the surrounding material without damaging the object.

A number of variations which are possible in the powder based LOM process and apparatus are discussed in the present invention. Different powder based materials, changing the sequence of process steps or omitting some of them altogether, different types of concentrated energy or matter means, different ways of introducing the change of property into the powder, and different ways of utilizing it in the object separation process, possibility of using cover gasses and liquids, and a variety of post processing techniques are considered.

The most significant limitation of the process is the shrinkage resulting from the internal stresses introduced into the object during the lamination forming step. This problem can be overcome by creating thin walled boundaries encapsulating the material of the object during the laminating process and then postprocessing the object in a furnace. Another way to reduce internal stress is to maintain the partial object during construction at a temperature just below the temperature where property change occurs. After the object is completed, the temperature is gradually lowered, giving any internal stresses time when the object may be semi-plastic to relieve themselves. A variety of other methods capable of reducing the effect of the problem on the dimensional properties of the LOM created object are discussed.

A number of details related to different elements of the LOM apparatus are discussed in the present invention. Ways of achieving desired thickness of powder layers, different methods of depositing these layers, a variety of ways for moving the platform (linear stage, rotary table, conveyor, etc.), methods of compressing the powder and scanning its surface with an energy beam are considered.

In another preferred embodiment, a supply station houses a supply of thin sheet material. The thin sheet material is fed into the system by suitable means and then is transferred to a laminations forming station where the patterns of desired cross-sections are cut by a laser beam manipulated by a positioning table plotter arms, mirrors, or a scanner. The cutting can be accomplished through traversing the laser beam around the periphery of a cross-section in a plotter-like manner or by removing the material in the areas surrounding a cross-section by a raster scanning process performed in a laser printer-like manner. The cross-sections can be formed on the object or separately. Later, if necessary, laminations are separated from the surrounding material and are transported to a stacking device where they are attached to the stack through adhesion, welding, brazing, or diffusion bonding techniques.

An improved method of production of a part by the sheet LOM process relies on a different sequence of steps in the LOM cycle. In that method, the attachment of the sheet material to the laminated stack is done first. Then it is followed by a forming step which is performed by a laser beam cutting the material. With multiple passes at, differing speeds, laser powers, or focus sharpness, less than one thickness can be removed to inwardly bevel an edge to correspond to a highly sloped region of the object. Bevels can also be created if the beam is controlled on more than two axes. The attachment can be performed either over the whole area of the laminated layer or selectively within the boundary of the cross-section. In the case of selective attachment the same or another laser beam can be used for welding the cross-section to the stack prior to the cutting. The laser beam can also warm an area so that its temperature reaches a bonding temperature with the application of a more generalized source of bonding heat to the exclusion of cool, non-laser warmed areas. Large objects can be lightened by totally ablating inner areas of the laminations so that one or more internal voids are formed. These voids can just be simple holes or complex supporting structures, examples of such being isogrid and honeycomb structures. A printed image of a negative of a cross-section produced on the sheet material itself or on an overlaying sheet can also be used as a mask in conjunction with a UV curing technique to selectively bond a cross-section to the laminated stack.

The possibility of using multilayered sheet materials, different methods of separating the extra material from desired laminations, the possibility of combining laser cutting and chemical etching processes in the lamination forming step, and other apparatus improvement possibilities are suggested.

Also considered is a possibility of combining certain features of powder and sheet based LOM techniques into a single device. This device will be capable of performing both powder and sheet based processes separately or simultaneously. The need in such device is caused by the desire to combine advantages of each method. On the one hand the sheet process is affected by heat caused warpage to a much lesser degree than the powder one. On the other hand noncontiguous contours may be a problem in some geometries created by the sheet technique while in the powder technique they are always supported by the surrounding powder. The possibility of filling the spaces created in the laser formed sheet cross-sections with a curable liquid plastic material are also discussed in the description of this version of the LOM apparatus.

The method and apparatus of the present invention has many advantages over currently used methods and apparatus for producing small batches of parts. The designer can work directly with the computer using the LOM system interactively for creating prototypes and verifying his concepts. Dies and molds can be manufactured inexpensively by the LOM apparatus. Highly complex metal matrix or composite parts can be produced for automobile and aerospace industries. Three dimensional maps can be produced for civilian and military applications. Artificial bone implants and prosthesis custom fitting individual patients can be created for medical applications. Optical lenses with complex surfaces can be investment cast from the patterns created by LOM technique. EDM and ECM dies, wind tunnel models, molecular models, and even art objects can be produced.

Parts of unlimited complexity, including those with sculptured surfaces, internal voids, and intricate channels, can be manufactured. No mills, drills or cutters are required. Production may be accomplished using one machine which uses one cutting tool—the laser. Setup time for different parts produced out of the same material is cut virtually to zero. It is no longer necessary to plan manufacturing procedures since parts are produced directly from computer generated images without involvement of the operator. Production cycles for complex parts can be reduced from weeks to minutes. Costs and use of skilled labor can be cut dramatically. For extreme precision, the three-dimensional objects can be constructed just slightly oversize, and then quickly finished to close tolerances with a conventional NC machining center.

The above and other advantages of this invention will be apparent from the following more detailed description when taken in conjunction with the accompanying drawings of the illustrative embodiments.

BRIEF DESCRIPTION OF DRAWINGS

FIG. 1 is a diagram illustrating different steps of the LOM process including powder deposition, powder compression, and cross-section forming;

FIGS. 2 and 2A are cross-sectional views of the apparatus for forming three-dimensional objects using the powder based version of the present invention and a reciprocating carriage concept for moving the laminations carrying platform;

FIG. 10 is a cross-sectional view of the apparatus for forming three-dimensional objects using a powder based version of the present invention and a rotary table concept for moving the laminations carrying platform;

FIG. 11 is a cross-sectional view of the powder based LOM apparatus utilizing the concept of a powder depositing device moving relatively to a stationary laminations carrying platform;

FIG. 12 is a cross-sectional view of a system of powder compressing rollers connected with a ribbon;

FIG. 13 is a cross-sectional view of a magnetically or electrostatically charged roller depositing a powder layer onto a platform and compressing it at the same time;

FIG. 14 and 14A are cross-sectional views from two directions of a powder based LOM system utilizing a stream of circulating powder during the powder deposition step;

FIG. 15 is a cross-sectional view of a powder based LOM system utilizing a steam of circulating powder and a moving roller during the powder deposition step;

FIG. 16 is a cross-sectional view of a powder based LOM system utilizing the concept of simultaneous and continuous powder deposition, compression, and energy beam scanning, with the material deposited on the flat surface of a cylindrically shaped laminate;

FIG. 17 is a cross-sectional view of a powder based LOM system utilizing the concept of simultaneous and continuous powder deposition, compression, and energy beam scanning, with the material deposited on the cylindrical surface of a cylindrically shaped laminate;

FIG. 18 is a cross-sectional view of a powder based LOM system utilizing the concept of the powder being, first, deposited onto plates of a conveyor and, then, compressed against the stack of powder laminations in order to become attached to the stack;

FIG. 19 is a cross-sectional front view of a powder based LOM system illustrating the method of powder deposition onto the laminations carrying platform by direct contact of powder in the powder container and the upper layer of the laminate;

FIG. 20 is a cross-sectional side view of a powder based LOM system illustrating the method of powder deposition onto the laminations carrying platform by direct contact of powder in the powder container and the upper layer of the laminate;

FIG. 21 is a cross-sectional view of a powder based LOM system demonstrating a method of powder compression by pressing the upper layer of the laminate against a stationary flat platform achieved by elevating the linear stage on which the laminate is located;

FIG. 22 is a cross-sectional view of a powder based LOM system illustrating the method of forming a thin layer of powder on the upper surface of the powder laminate by slicing that layer with the lower edge of powder container as the laminate moves relatively to it;

FIG. 23 is a cross-sectional view of a powder based LOM system illustrating a lamination forming operation accomplished by selectively changing a property of the powder layer pressing against a transparent flat window with the laser beam shining through that window;

FIG. 24 is a cross-sectional view of a sheet based LOM system illustrating the possibility of combining the powder and sheet LOM processes into one system;

FIG. 25 is a cross-sectional view of a stack of sheet laminate on a vertically movable platform with a noncontiguous portion of a lamination supported by a flowable material deposited from the powder container of the combined sheet-powder LOM apparatus and filling the empty spaces within the formed sheet laminations;

FIG. 26 is a cross-sectional view of multilayered sheet material used in the laminating process, where either primary thicker layer or secondary thinner layer is ablatively removed during the laminations forming step;

FIG. 27 is a cross-sectional view of a powder based material with spaces between particles filled with a liquid of powder bonding agent used for bonding powder during laminations forming step of the powder process;

FIG. 28 is a cross-sectional view of a part formed by the powder encapsulation technique used to avoid warpage and deformation resulting from the energy beam heat effect;

FIG. 29 is a perspective view of a sheet laminate in which the extra material surrounding individually formed laminations is not removed during the laminating process, instead, it is cut in a cross hatching fission into multiple small portions easily removable after the laminating process is complete;

FIGS. 30 and 31 are cross-sectional views of a sheet laminate located on the laminations carrying platform where desired portions of a lamination are attached to the stack by an action of the laser beam and the extra ones are removed by a vacuum suction plate;

FIGS. 32 and 32A are cross-sectional views of a sheet laminate illustrating the possibility of attaching desired portions of a lamination by pressing previous lamination against an adhesive coated and cut new ones;

FIG. 33 is a perspective view of an ablatively formed lamination;

FIG. 34 is a perspective view of a periphery cut lamination;

BEST MODES FOR CARRYING OUT THE INVENTION

Figure 5:
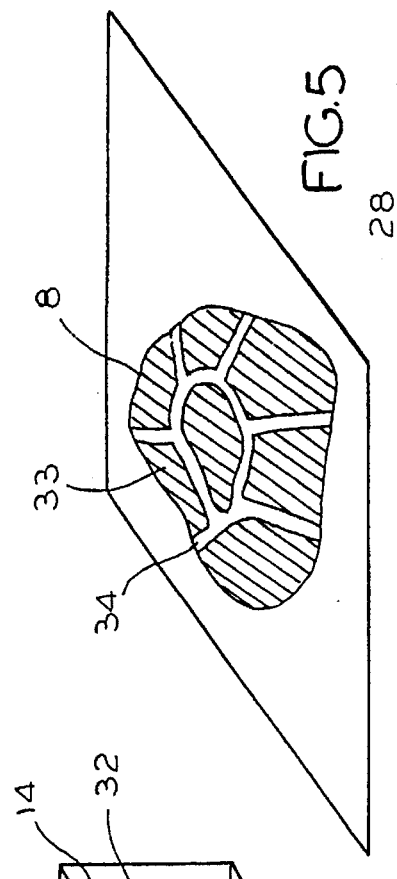
FIG. 5 is a perspective view of a lamination divided into a number of smaller portions in order to control internal stresses within the part during the laminating process.

Instead of cutting extra material out of raw stock, like it is done in traditional machining methods, the laminated object manufacturing (LOM) system builds the part by adding material to it in a controlled fashion. First, a digital computer model of a part is created with suitable 3D computer aided design (CAD) software in a computer. Then the model is examined to determine what orientation would be most easily duplicated by the LOM System. Generally, the largest, flattest surface is used as the base of the LOM object. However, some slopes are more efficiently and precisely constructed if they are oriented with most of these flat surfaces vertical. Next, the computer model is cut into slices by the computer. In the simplest form of the invention, the slices are between parallel cross-sections located 0.001"–0.030" from each other, the slice width being chosen to match the thickness of the material to be added for each slice. For areas where there is little change in object shape from slice to slice, thicker slices can be generated and thicker materials employed. For areas with large shape changes or when high precision is desired, the slope of the edges of the slices can analyzed and the shape of the slices be adjusted to improve the shape of the final object. Generally, it is preferable that slice shapes are determined and then cut, since modern computers are fast enough to control cutting and calculate the shape of the next slice concurrently.

Two major groups of materials which can be employed in the LOM process are covered by the current application. The first group consists of flowable materials, i.e. powders, powder based slurries or pastes, and some liquids. The distinction between the powder based slurries or pastes and liquids lies in the fact that liquids are incompressible. Powders on the other hand are highly compressible because the particles thereof normally have substantial open volume in the form of spaces between them. If these spaces are only partially filled with liquid, then the mixture will retain some powder qualities such as compressibility and therefore is not to be considered as a liquid but rather as a powder based material. As the powder becomes more saturated with liquid, its properties become more liquid like and less compressible. The second group of materials used in the LOM process are sheet materials such as metal foils and metal, plastic, ceramic, organic, and composite sheets.

A powder based LOM process is shown in FIG. 1. It builds a three-dimensional object by replicating an earlier generated computer model by, first, spreading a thin layer of powdered material (1) on a platform (2). Later, the powdered material is compressed with a flat surface by the action of a roller (3) running over the powder within a controlled pressure range. At this point some bonds between the particles of the powder are formed and the layer (4) gets attached to the platform (2) or the underlaying layer. Although the bonds are fairly weak, the material (1) stays attached even if the platform (4) is turned upside down.

At this stage the geometrical information about the first slice of the object (6) is transmitted from the computer to the scanning component of the system which functions like an automated laser printer. It differs from the traditional paper printing devices by its ability to manipulate much more powerful laser beams, such as YAG or $CO_2$ laser beams.

Next, the printer scans the surface of the powder with a focused laser beam (7) in the pattern of the desired cross-sectional slice (8). Note that the beam (7) is shown with a noticeable focus angle. As will be described hereinafter, the focus angle may be employed to cut, bond, or fuse so that edge bevels are formed on the slices (8). The printing operation creates a strong bond between the particles of the powder which belong to the cross-sectional slice and any adjacent slice. Preferably the platform (2) and the environment thereabout is controlled at an elevated temperature just below the fusion, sintering, welding, or softening temperature of the powder. This reduces any internal stresses created in the object (6) and enables the laser beam (7) to be moved at a high velocity since it only needs to provide a small amount of energy to raise the temperature of the powder to its bonding temperature.

Next, the platform is returned into its initial position. The process is repeated until all of the slices are deposited, compressed, and "printed". The block of material created as a result of the laminating process resembles a sand casting within a sand mold, with a weakly bonded and fragile "green state" powder (5) surrounding strongly bonded object (6) which replicates the computer generated model. After that, the block of material created on the platform (2) is slowly cooled to reduce the formation of internal stresses and then subjected to an impact or vibration. As a result, the extra material (5) previously unaffected by the laser beam (7) falls off, releasing the part that replicates the computer generated model. For thin, weak, and lightly connected objects, buttresses can be formed in the extra material (5) to assist in maintaining the dimensional stability of the object (6) until it is completed, at which time the unaffected powder material can be removed and the buttresses can be removed by cutting them off with the laser or mechanically removing them.

There are a number of ways in which the process and the apparatus performing it can be implemented. For example, there are a number of powder based materials that can be used, such as plastic, metal, ceramic, or composite. They do not have to be pure powders and can in some instances contain certain amount of liquid phase material. Usually, most of the liquid phase material will be eliminated during the process or after its completion by evaporation or absorption etc. FIG. 27 illustrates a powder based slurry with the adhesive component (64) consisting of a liquid or a powder that fills the spaces between powder particles (63), which are in contact with each other. A mix of metal or ceramic powders and the adhesive component can be laminated, with the adhesive component (63) eliminated by evaporation during or after the process. Also, the material can be preformed by press-rolling or press compaction into thin sheets of "green state" powder to be used in the laminating process.

Other variations of the process involve changing the sequence of the steps of the process or omitting some of the steps altogether. The basic steps of the process are: create the computer model of the object; slice the model by the computer; deposit powder based material; layer level; compress; create a layer of a cover gas or a liquid; "print" the slice; remove the extra material, and post process to improve the structural and surface qualities of the object.

One of the known variations is to skip the powder compression step altogether when producing light weight, light duty, thermoplastic parts and proceed with the printing step. The printing step is accomplished with a $CO_2$ laser used to fuse the particles of uncompressed thermoplastic powder. This step can be followed by a compression step to achieve better properties of the final object. However, if the time and expense of a compression step are to be expended, a better process is to do the compression before the fusing.

The type of the concentrated energy means used in the printing process can also be varied. Lasers of different wavelength with continuous wave or pulse characteristics, nonlaser light, particle beams consisting of electrons, protons, or other high energy particles, microwave energy, and heat generated by electric current can be used. These energy means usually include means to concentrate the energy on the surface of the powder based material during the printing step. The concentration usually will be performed by a focussing lens or a mirror, or by forming energy or particle beams of very small diameters.

Another possibility is to substitute concentrated jets of matter for the concentrated energy means during the printing step to chemically change or mechanically bond the material within the pattern of the slice. The main purpose of the printing step is to create a difference in mechanical or chemical properties between the material which belongs to the slice and the material around it. This difference is used in the process to separate the finished object (6) from the surrounding material (5).

Usually the difference is expressed in the strength of the bond between the particles of the powder. The powder affected by the printing means usually will have stronger bonds and be less fragile than the unaffected powder, but such is not always the case. For example, a printing process similar to printing a negative of a picture can take place where a portion of the compressed powder layer that surrounds the cross-section to be defined is rapidly heated by the energy means in the presence of air or another oxidizing gas or a liquid. This heating causes oxidation of the particles of the layer and weakens the bonds between them. Later a laminated object printed in this manner can be sintered in a sintering furnace. This will cause the previously non-oxidized powder, which belongs to the object, to form strong bonds while the surrounding oxidized material will remain weakly bonded and will easily separate during the separation step.

A chemical change can take place during the printing step. That change also can be utilized during the separation of the material surrounding the object. A combination of chemical and mechanical changes can be utilized during separation. For example, if the particles of the compressed powder are heated, compacted, or otherwise affected by the printing means, the pores between them become much smaller than the pores of the unaffected powder and sometimes they disappear altogether. Therefore, if there is a solvent that is used for the removal of the extra powder, it will penetrate and dissolve the powder surrounding the object much faster than the object itself.

Figure 9:
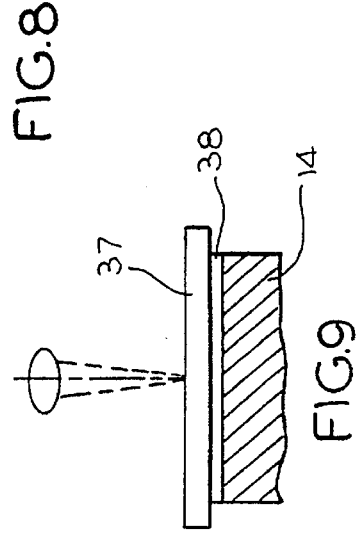
FIG. 9 is a cross-sectional view illustrating a laser compaction technique for changing properties of the powder.

Another way to introduce the change is to utilize laser compaction (FIG. 9). In this method a thin layer of liquid (38) is introduced on the surface of the compacted powder (14). Sometimes this layer (38) is covered by a piece of material transparent to the laser beam (37). When the printing takes place, this liquid rapidly evaporates creating extremely high pressures on the surface of the material. This causes it to compact and create frictional or deformation bonds between its particles.

The mechanical separation of the extra powder material can be accomplished in a number of ways. They include impacting the block of material with a mallet or a hammer, vibrating, grid blasting, cavitating, ultrasonic cleaning and other means. The separation can be assisted by increasing the difference between the properties of the object and the surrounding powder after the object has been completed.

For example, a block of metal laminations that has been created as a result of the laminating process can be treated by a chemical, which will relatively quickly penetrate the surrounding powder, weakening the bonds between the powder particles. Another way to accomplish this weakening is to put the object in a furnace containing an oxidizing atmosphere, thus burning or oxidizing the particles of the surrounding powder. Another possibility is to increase the difference for each layer separately during the performance of the process by first printing the slice and then introducing a reactive gas or a liquid above the surface of the layer and heating the entire surface to cause the desired weakening of the bonds of the surrounding material.

Sometimes, in order to assist the creation of the desired difference during the printing step, a cover gas is used over the heated surface. This is usually done to prevent oxidation and to reduce the oxides that exist on the surface of the powder particles. These gases can be inert or ones that do not react with the particular powder material. They can also contain reducing agents such as hydrogen and include the gasses that are usually applied during conventional powder metal sintering processes.

Figure 8:
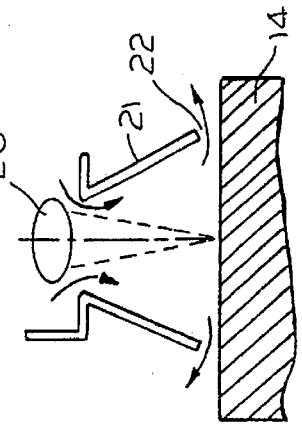
FIG. 8 is a cross-sectional view of the stack of powder laminations with a cover gas or liquid channeled over its surface through an enclosure extending from the energy beam directing device to the surface of the laminate.
Figure 7:
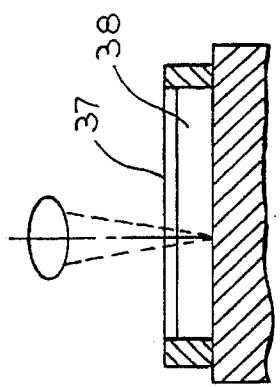
FIG. 7 is a cross-sectional view of the stack of powder laminations with a cover gas or liquid channeled over its surface through an enclosure with the surface transparent to the laser light.

The gas can be directed towards the surface of the part with a nozzle or be circulated above the surface of the part within an enclosure (FIG. 7). This enclosure can be a rectangular channel with a piece of a sheet material (37) transparent to the printing beam located above the upper surface of the laminated part (14). The need for the transparent material can be eliminated (FIG. 8) by extending the enclosure (21) from the scanner (28) directing the printing beam to the surface of the part (14). In this version the cover gas is introduced at the upper portion of the enclosure (21) and is either contained within it during the printing or is allowed to escape through small openings (22) between the bottom of the enclosure and the part (14). Another way to protect the powder against oxidation is to perform the printing step in vacuum.

After the object has been obtained by separating it from the surrounding powder, a number of postprocessing operations can be performed on it to achieve the desired structural and surface properties. A grainy or step-like surface of the object can be finished and coated by conventional means, the object can be heat treated, recompressed or HIPed to reduce its porosity. Its pores can be saturated with another material.

There are a number of problems associated with the printing on the powder layers using concentrated energy or matter means. One of them is shrinkage. Another is internal stresses and associated warpage created by changes caused by printing means that consolidates the powder. The shrinkage and warpage can be controlled by applying high pressure compaction forces to the powder before the printing step, thus causing stronger bonds between the green state particles that resist internal stresses causing warpage and shrinkage. However, these strong bonds can negatively affect the ease of separation of the extra material after completion of the laminating process by making the powder separation excessively difficult or even impossible. Therefore, an optimal range of compaction pressures, which differs from powder to powder, usually exists.

Figure 4:
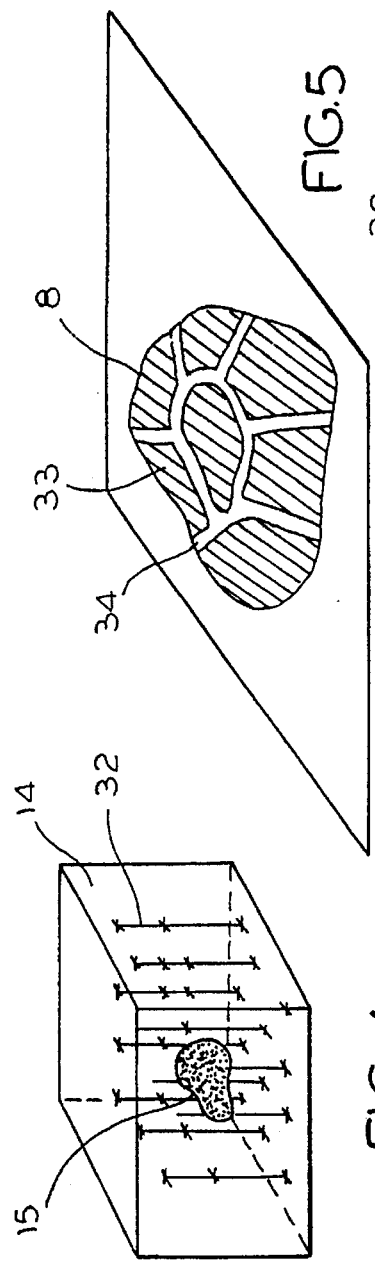
FIG. 4 is a perspective view of a part created by the powder LOM technique surrounded by extra material and supported by a support network.

One way to combat the shrinkage is illustrated in FIG. 4. The printing means are used during the lamination process to create a network of wires (32), which is usually independent of the shape of the created object (15) and spreads throughout the object and surrounding powder in a manner similar to the metal structure supporting reinforced concrete.

Figure 6:
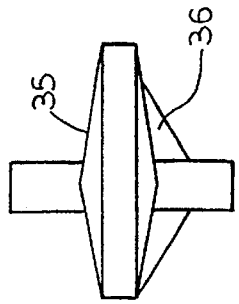
FIG. 6 is a planar view of a product part containing support ribs in order to control internal deformations within the part during the laminating process.

Another way to control warpage (FIG. 6) is to introduce draft angles (35) into the portions of the part that are parallel to the laminated layers. Still another way is to support these portions with ribs (36). The shrinkage can be accounted for by oversizing the part, using computer software techniques similar to the techniques used to compensate for shrinkage in conventional plastic molding or die casting.

A promising technique for controlling the warpage is illustrated on the FIG. 28. It shows an object created by the laminating process where instead of affecting a total cross-section of the object during the printing step, the printing means fuse the powder along thin lines defining the periphery of each lamination. These lines are integrally bonded to each other during the laminating process to form a shell (65) encapsulating the rest of the powder material (14), which belongs to the object. Later, the object defined in this manner is separated from the surrounding material and is cured in a furnace or is subjected to a source of curing radiation to cause fusion of the encapsulated material. The powder material (64) may be chosen for its dimensional stability and the object constructed slightly undersized. Thereafter, the object can have its exposed surfaces metalized to net shape. Then the previously powder material is removed from the metal shell so formed and the metal shell is filled with metal or other robust material so that a robust object results. The metalization tends to smooth any undesired lamination roughness of the object's surface.

Besides powder based materials, the LOM process can utilize sheet materials to create three-dimensional objects. The basic steps of the sheet based LOM process are similar to the powder based techniques. Just like in the powder processes, they include a step of generating cross-sectional slices from a three-dimensional computer model and repeated steps of depositing the material comprising a single lamination, forming that lamination by printing means comprised of concentrated energy or matter, separating the material that belongs to the slice of the object from the surrounding material, and attaching that material to the stack of other laminations comprising that object. Therefore, many aspects and claims of the current application are common for both powder based and sheet based processes.

The cross-sectional slices can be defined by either ablative removal (FIG. 33) of areas (71) of the sheet material (60) in a raster fashion or by cutting that material (60) in a vector fashion (FIG. 34) around the periphery of these slices. Usually the concentrated energy means used for the slice definition will be comprised of a laser beam manipulated by a laser scanner. Another possibility is to use an electron beam or a liquid jet cutting technique.

The raster based ablative removal approach has the advantage of making the processes of a slice definition and the removal of the material surrounding it simultaneous. However much greater energy expenditures are required because the material surrounding a cross-section has to be evaporated or burnt away. Generally the speed of the process is limited by the output powers of the available lasers, which can be an order of magnitude more expensive each time output power is doubled. Therefore, vector or line "printing" is a faster, more efficient process for organic materials such as paper, foam, or plastic sheet.

Sheets used in the process can be comprised of several layers of different materials. Usually one layer, which is called primary, is at least five times thicker than another or others attached to it. For example: this primary layer could consist of precompressed "green state" powder while secondary layers attached to it could be made of an organic sheet material; the primary material could consist of an organic sheet attached to a very thin layer of metal foil; the primary could consist of strong fibers coated on one or both sides with a bonding resin; the primary material could be a metal foil coated by an organic material; or the primary material could be any sheet material coated with an adhesive.

One of the important differences between the sheet LOM process and the powder LOM process is that sheet laminations do not disintegrate if formed separately from the stack. Therefore, some or all of these laminations can be laser cut or formed by multiple other means prior to the attachment thereof to the stack to speed up the construction of the object. Thicker laminations can be used where there is little difference between adjacent laminations to further speed up the process.

For example, if formed laminations consist of the primary metal or ceramic sheets coated with plastic or a metal with the melting temperature lower than that of the primary material, then these laminations can be joined together by heating the entire stack to a temperature higher than the melting temperature of the secondary material but lower than that of the primary material. Another way to accomplish bonding of multiple laminations into a three-dimensional object is to use diffusion or eutectic bonding processes.

Although laminations usually are formed after placing material comprising them onto the stack, since this assures registration of adjacent laminations, their formation can take place at different locations than the laminations carrying platform. This assists in preventing temperature differences otherwise created by the concentrated energy means employed in the lamination forming process.

In cases where sheet material employed in the process is a multilayer material, the formation of a lamination by printing means can be accomplished by cutting or ablatively removing (FIG. 26) the primary material (68) without affecting the secondary material (69). For example, a foam sheet laminated with a secondary material such as thin metal foil can be evaporated by a laser beam without affecting the thin metal foil to a significant degree. The advantage of this technique is that non-attached pieces of a cross-section comprised of the primary material are held stationary with respect to each other by the secondary layer. After the formed laminations have been joined together by adhesive bonding, the stack can be placed in a selective etching bath where the exposed portions of the thin metal foils are etched away without affecting the foam.

Another example of a combined use of a chemical etching and laser forming technique can be considered by selecting a multilayer material comprised of a metal foil as a primary material, coated or laminated on both sides with an organic material that can be selectively ablated by a laser beam to expose areas of metal that thereafter can be selectively chemically etched to complete the formation of laminations for subsequent joining into a laminated object.

Adhesives can be advantageously used as secondary materials in the LOM process. The sheets can be either precoated with an adhesive or they can be coated by it during the laminating process. A precoated adhesive can be in the dry form so that it can be activated by wetting during the laminating process. The adhesive can also be of a kind activated by an UV or infrared radiation.

An important and usually difficult problem, which needs to be resolved in the LOM process, is how to remove the material that does not belong to the laminated object. Material removal becomes especially difficult for slices of a laminated object that consist of several relatively noncontiguous portions. Another question to consider is when to remove the extra material, i.e. during the laminating process, or after. Sometimes (FIG. 25) the unremoved material (61) serves a useful role by supporting portions of laminations (62), which belong to the laminated object (15) that otherwise would hang in the air or be misplaced. The extra material can also stabilize the object during a cooling down or annealing process step.

Several possible sequences of lamination assembling have been suggested in my earlier U.S. Pat. No. 4,752,352. They included a technique of sequential cutting portions of a given layer that do not include any other contours within themselves and either attaching them to the stack or discarding them. Another suggested technique is to join noncontiguous portions of a given lamination with thin strips of material, which are removed after the laminating process. A number of different approaches are possible. The simplest one is to perform ablative removal of the extra material during the lamination forming process, thus, simultaneously forming laminations and getting rid of extra material. Another possibility is to use vector cutting around the periphery of cross-sections of the laminated object, but not removing the extra material as the laminations are placed on the stack. In this case, the extra material has to be prevented from being strongly bonded to the laminated object.

If an adhesive attachment is used, then computer means can be instructed to, first, reduce the amount of power delivered by the laminations forming laser and then to selectively burn, dry, cure, or deactivate at least some of the secondary material or adhesive which would otherwise be responsible for attachment of the extra material to the laminated object. The same (FIG. 30) layer forming laser beam (7) can be manipulated in a different manner to selectively activate the adhesive properties of a secondary or even primary layer within the portions (62) of the vector cut layer that belong to the laminated object (15). For example, spot or contour braising or welding can be performed for the needed portions while leaving extra material unaffected. This extra material (FIG. 31) can be removed by a vacuum platform (56) from the stack.

Another possibility (FIG. 29) is to, first, contour cut each lamination in a vector fashion and then cut the extra material of the layer into multiple small pieces (67) in a crosshatching fashion. These pieces can be attached to the stack at the same time as the needed material and, thus, they will form a support structure for the laminated object. Later the extra material, although attached to the object (66), but relatively weak in strength, can be removed by mechanical means.

Still another way of separating extra material from the laminated cross-sections of an object is to utilize the fact that most of the thinly sliced cross-sections of an object display a gradual variation in their geometry. Sudden differences in the geometry are a relatively rare occurrence (FIG. 32). Therefore, if a cross-section (71) has been formed and attached to a stack and the next one (62) does not display sudden changes in the geometry, and if it does not have portions to be discarded that overlap areas of the previous cross-section, then it can be attached to the previous layer by pressing it against the new layer coated with adhesive. Only the needed portions (62) of the layer will come into the contact with the previously attached lamination and will be picked up through the use of the adhesive force while the unneeded material will remain on the platform (56). The platform (56), which positions and places a lamination against the stack of laminations, can be a piece of material transparent to the laser beam or it can include a vacuum or a magnetic pick up mechanism.

The question of how to support noncontiguous portions of laminations during the laminating process, or how to support structurally weak portions of the laminated object during that process can be resolved by including into the laminating sequence (FIG. 33), a step of filling the space (71) bounded by the thickness of a formed lamination or several formed and assembled laminations with a flowable material. This material could be a powder, a powder based slurry, a very viscous liquid, or a curable liquid.

If a powder is used, a step of its compression can be included in the laminating sequence. This step can be performed for each layer separately or for several layers simultaneously. Similarly, for a curable liquid used to fill the space bounded by the laminations, a step of exposure to the curing radiation can be included in the laminating sequence.

At the design stage, the created geometry of the laminated object can represent a mold surrounding the space of a castable object to be produced. In this case the flowable material fills in what will be the castable object and therefore, the stack of laminations surrounding it is removed after the laminating process is complete.

In other cases the flowable material is used only to support laminations during the laminating process and therefore, it is removed after the process is complete.

The flowable material used in the process also can be a liquid ceramic, which after curing serves as a mold in a lost wax or a lost foam process after material comprising sheet laminations is removed out of it through melting, vaporization, or burning. It is also possible to perform lost material processes after an object has been created by the powder based or sheet based LOM techniques, using that object as the lost material in the process.

The flowable material can fill the space within the laminations by flowing it onto one or several laminations and then scraping the excess with a scraping edge moving on the upper surface of this layer or layers.

As should be evident from the above, there are two principal types of machines capable of performing LOM processes: machines that form the material of a lamination after it has been attached to the stack and ones that form it before it has been attached to the stack. Each type has its own advantages and disadvantages. The type which cuts shapes in the laminations after they are attached to the stack has a lesser chance of misplacing object slices with respect to each other, since their relative positions are established by the beam positioning device (scanner or XY table) only. High precision of registration of layers and the simplicity of the device are the main advantages of this approach, but another benefit comes from avoiding warping of the laser cut material supported by the structure of the stack. A disadvantage of cutting on-stack is that it is more difficult to get rid of the waste material from the desired material in each lamination than when the cut-off-the-stack method is used.

The attachment between laminations in the stack can be assisted by a hot plate or a hot roller if a heat sensitive adhesive is coated onto the sheets used in the process. Also the entire environment including a warm plate or warm roller can be maintained just below the adhesive activation temperature and the laser defocused and scanned across the lamination to raise the temperature above the adhesive activation temperature. A warm roller is preferred, because the scan can occur just ahead of the roller. If desired, the scan can be in a selective pattern so that only parts of the final object are bonded together. The waste of a lamination can be left unbonded, or just selected small regions thereof, such as dots can be bonded. This partial bonding or non-bonding greatly reduces the difficulty of removing waste material when the cutting on-stack method is used. An ultra violet lamp can be used to bond sheets together if a UV curable adhesive is used.

In the cut-on-the-stack technique, the sheet is cut by the cutting beam after being put into the contact with the top lamination of the stack and in some cases (although not necessarily) attached to it. The beam power is adjusted to preferably cut the material to the depth of one lamination.

One way to facilitate separation of the material surrounding the laminated object is to cut parting lines in the portions of the material surrounding object's cross-sections during the cutting step of the laminating cycle. This way separation of the object from the surrounding material can be performed in the same manner as a mold is separated from a molded object. As opposed to the conventional molding processes there is no limit to the number of parting lines which can be established. Another way to separate the unneeded material is to cut material surrounding every slice in a cross hatching fashion into a large number of squares (or other shapes including 3-dimensional solid ones by occasionally ablating one or more laminations above a solid shape so that the next lamination does not become bonded thereto). The surrounding material formed in this manner can be removed easily by mechanical means or by dissolving it in a solvent into which the whole laminated structure is immersed for a short period of time. To make separation even easier, the size of the cross hatching can be made very small adjacent the slices and larger in areas spaced from the slices to support the object during its construction and reduce the amount of cutting required for material removal. In areas of particularly difficult separation, the laser beam (7) may be defocused to widen the vector cut line between the slices and the waste.

Figure 39:
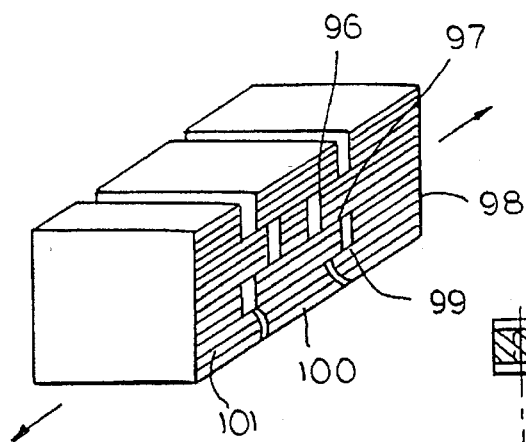
FIG. 39 is a perspective view of a part being separated from the surrounding material after the LOM process.

The following are some of the primary techniques which are considered for separating the material that does not belong to the laminated object. FIG. 39 illustrates how a laminated object (100) is separated from the unneeded portions (98) and (101). In order to accomplish the separation, an unbonded condition has to be achieved on portions of cross-sections (96), (97), and (99) where unneeded material overlaps the material of the part. This condition can be achieved in several ways, which will now be described in some detail.

Figure 38:
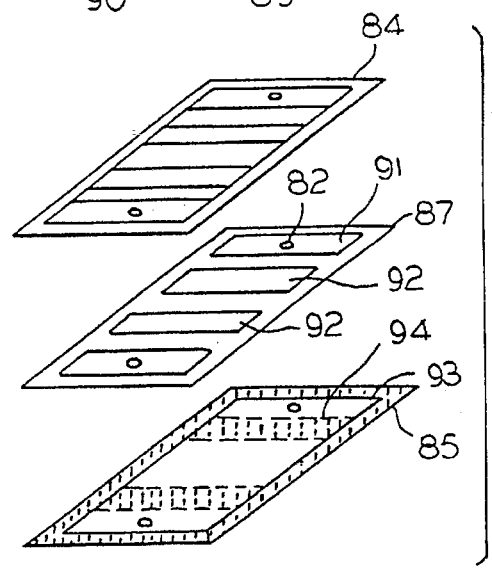
FIG. 38 is a perspective view of laminations bonded to each other using different attachment techniques and different provisions for the separation of unneeded material.

It is possible to use the beam of the laser to dry off or otherwise inactivate the glue on the portions of the previous layer that must not become attached to the new layer. This can be accomplished either before or after the attachment of the material that constitutes the previous cross-section slice onto the stack. FIG. 38 shows sequential cross-section slices (85), (87), and (84) of a part (81) shown on the FIG. 36. The cross hatched part of the cross-section slice (85) needs to be scanned with the laser beam in order to deactivate its adhesive and prevent its attachment to portions of the cross-section slice (87) that do not belong to the object being created. The area to be scanned can be established by Boolean subtraction of the next cross-section from the previous one. This way areas of the cross-section slice (85), which overlap portions (91) and (92) of the lamination (87), will not be scanned. Subsequent cross-section slice (84) can be cut around its periphery.

It is also possible to use the beam scanning in a manner described in the previous technique but with a power high enough to burn the material of the area being scanned so that an indentation is created which will prevent bonding of portions of the subsequent layer. This technique is especially useful when the glue is deposited on the side of the material facing the stack, but is restricted in that such material can not be extremely thin. When an indentation is created, the portions of the sheet material deposited on the top will not be in the contact with the material at the bottom and therefore will not glue to it.

It is further possible to cut the unneeded material before the sheet is attached to the stack. It is important to make sure the needed material stays attached to the sheet as it is done. The unneeded material is then suctioned off. Thereafter, the needed material is brought into contact with the stack, glued by pressing it against the stack, and cut off of the ribbon. This can be done either to eliminate unneeded material from layers or to prevent portions of some cross-sections from attaching to the others.

Figure 40:
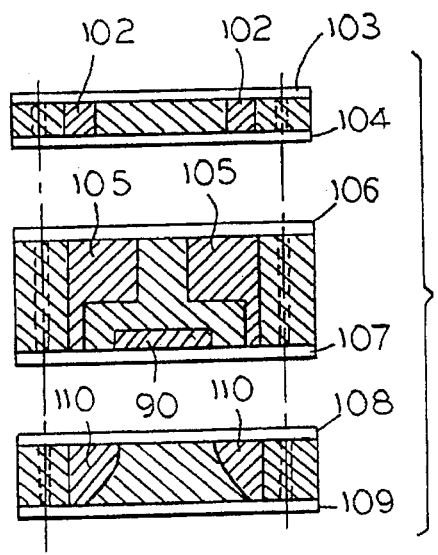
FIG. 40 is a cross-sectional view of a part laminated out of several slabs.

FIG. 40 illustrates another useful technique. The part being created can be divided into several slabs each of which can be easily separated from the surrounding material. These slabs can be created automatically by feeding partition sheets (103), (104), (106), (107), (108), and (109) onto the surface of the laminated stack when needed. After the part portions are formed, the partition sheets are removed and the part portions are connected to form the object.

Figure 36:
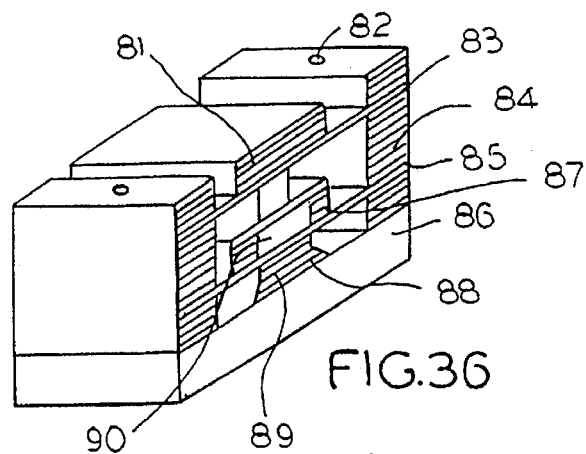
FIG. 36 is a perspective view of a laminated part supported by a vertical support structure laminated simultaneously with it.

It is recommended that an object being laminated should be surrounded by a support structure, which is grown simultaneously with it (see FIG. 36). The support structure has dowel pin holes (82) that also are cut in the process. Partition sheets are bonded to the stacks and sandwiched between them weakly enough to be easily separated. In the case of creating a part consisting of slabs shown in FIG. 40, the process might proceed as follows: first, remove the sheet (108) and put dowel pins through the holes (82) of the slab; next, remove unneeded pieces (110); then, remove the sheet (107) from the next slab; next, remove the unneeded material (90); then, glue the slab to the previous one; next, remove the unneeded pieces (105) and the sheet (106); then, remove the sheet 104 from the next slab; next, remove the unneeded pieces (102); then, attach the slab to the stack; and finally, remove the sheet (103) and the support structure.

Figure 37:
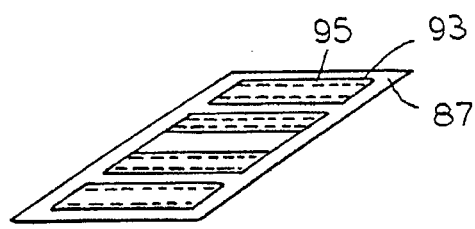
FIG. 37 is a perspective view of a lamination bonded by a selective bonding technique to a stack prior to being formed.

FIG. 37 illustrates how the cross-section (87) of the object (81) could be, first, bonded to the section (85) by moving a beam that activates bonding along dashed lines positioned within contours to be attached, and then cutting the material along solid lines. Corrections, taking into account the beam position and the diameter, shape, focus angle and/or velocity of the spot that the laser beam creates, should be made. For example: for a round spot from a narrow beam with relatively parallel sides, moving relatively slowly, add almost the entire radius of the spot to the center aim point to determine where the edge of the object will actually be cut or where the bonding will take place, if an edge bonding step is being performed. This is because the energy actually applied by a moving spot of finite size is relatively bell shaped in cross section. If enough energy is provided to cut through a lamination at a side edge of the spot, the energy at the center is enough to undesirably cut an underlaying layer. The cutting should be performed to the depth of a single lamination. The unneeded material could subsequently be vacuumed off or left on the stack for the future removal. Note that if suitable adaptive optics can create a square spot or a ring spot, a side of which is maintained as a chord of the slice, more precise slices can be cut because the actual cut edge is more predictable. Also, if wide angle beams are used (ones that have an appreciable angle between opposite sides), it is possible to create a positive bevel on the edge if the beam is sharply focused at the lower surface of the lamination and a negative or undercut bevel if the beam is sharply focused at or above the upper surface of the lamination, resulting in a smoother surface finish on the object. The smoke caused by such cutting that remains within the cut, defocusses the laser energy and helps control the depth of cut.

FIG. 36 shows a possibility of creating a vertical support structure (84) consisting of stacks of material surrounding the part and laminated simultaneously with it. In order to support cantilever portions of suddenly expanding cross-sections (81) and (87), supporting layers (83) and (85) are created during the laminating process. Perforations through the support layers (83) and (85) are cut by the laser beam around the periphery of cross-sections of the object corresponding to the levels of the supporting layers in order to facilitate the separation of the support structure from the object after the completion of the laminating process. An immersion of the object with the support structure into an etching bath as well as mechanical means could be used to separate the laminated object from the support structure.

In the case of metals, bonding can be performed by a laser or an electron beam to weld, braze, or eutecticly bond. In the case of plastics, in addition to the cutting laser beam, a second UV laser beam could be used for selective activation of a UV adhesive coating the sheets. Also, $CO_2$ or YAG beams could be used for activating a heat sensitive adhesive. In the case of metals, these beams could selectively braze or solder metal foils used in the process.

Activating energy assisted selective bonding of the material that belongs to the laminated object can also be accomplished by illuminating glue coated sheet material with activating energy (e.g., light of a UV lamp) through a mask printed either on the material itself (if it is transparent to the activating energy) or on a separate sheet media. Also, the glue itself can be deposited by printing it onto the sheet within the areas of slices to be bonded. A more detailed description of these techniques will be given in the description of the sheet system.

The system capable of selective bonding can be used to laminate a three-dimensional object out of more than one material by either supplying different materials for different laminations or even by supplying different materials for a single lamination. If the materials are fiber reinforced composite, then the orientation of the fiber can be changed from layer to layer. With the latter, aligned "Z" direction holes can be formed in the slices of the object for insertion and bonding of Z fiber reinforcement as a post processing step. The materials that comprise a single lamination can be attached to the adjacent lamination by sequentially performing the selective bonding step for each of them, followed by the lamination forming step outlining the area comprised of that material, followed by the removal of the material surrounding that portion of the lamination.

Just as there are many similarities between the powder and the sheet based LOM processes, there are a number of similarities between the automated systems which implement them. Therefore, many features of the powder system are present in the sheet apparatus.

The preferred embodiment of the powder based LOM apparatus is shown on the FIG. 2. This embodiment incorporates a powder carrying platform (2) located on a vertical stage (16). The platform (2) and the laminated powder layers (15) located on it are surrounded by an enclosure (17) whose walls are perpendicular to the laminated layers (15). The platform (2) moves within the enclosure (17) like a piston within a cylinder. The enclosure (17) is necessary to prevent the breakage of the powder part during the compression operation. It also helps to define the outer periphery of the laminated layers. In order to reduce the friction between the laminated powder layers (15) and the enclosure (17), an open end or closed loop ribbon (9) can be introduced between them.

The enclosure (17), which also supports the housing of the vertical stage, is attached to a carriage (18) traveling reciprocally on two linear slides (31). The enclosure (17) is located between the slides in such a manner that the distance (30) between the top of the enclosure (17) and the slides is much smaller than the total height of the fully extended vertical stage. This condition helps to reduce the bending moment applied to the slides during the compression operation and prevents wedging of the carriage (18) on the slides.

Figure 3:
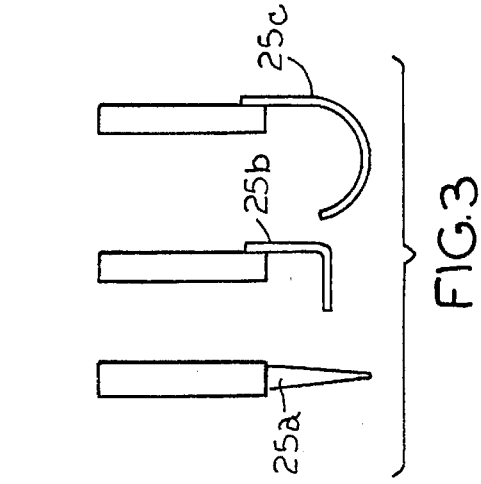
FIG. 3 is a plan view of scrapers used in the powder leveling step.

The cycle starts by moving the platform (2) at a constant speed under the powder container (12). At this point the powder flow from the container (12) is started by a linear actuator (10) opening the gate (11) covering the slot located at the bottom of the container (12). The flow can be helped by a feed mechanism located near the slot. The layer of the deposited powder may be somewhat uneven at this point. It is flattened by the scraper (25) removing the excess of the powder from the part, which continues its linear movement. The shape of the scraper (25) can vary depending on the application. Several possible shapes, including the straight edge (25a), flat bottom (25b), and curved bottom (25c) are shown in FIG. 3.

The thickness of the deposited powder layer is regulated by the movement of the vertical stage (16), which establishes desirable distance (47) between the deposited layer to the upper edge of the enclosure (17), should be made as small as possible to assure good support of the layers by the enclosure and to create a correct outline of the layer's periphery.

As the linear movement of the carriage (18) continues, the deposited powder layer is compressed by a stationary roller (3). The pressure of the compression is regulated by the relative distance (13a) between lower portion of the roller (3) and the deposited powder layer and is monitored by the force sensor (26). This distance is regulated by the movement of the vertical stage (16). A system of rollers (3a) (FIG. 12) can be substituted for roller (3). The rollers (3a) may be covered with a ribbon (48) which forms a less than 20° angle (40) with the compressed layer (1).

Continuing its movement, the part goes under the vacuum cleaning device (20), which suctions the extra powder that has been removed by the scraper onto the upper surface of the enclosure (17). The powder is transported by the moving air steam to a powder separator (13) located above the powder in the powder container (12). The cyclone or a screen type separator (13) returns the extra powder back into the powder container (12).

If it is necessary to introduce some liquid on the top of the compressed powder layer, it is sprayed onto the surface of the laminated part from the nozzle (24) as the carriage (18) continues its linear movement. Moving further, the carriage (18) gets under the laser scanner (28) that steers the beam (7) produced by the laser (29). At this point the cover gas is supplied from the hose (27) into the enclosure (21). During the portions of the cycle when the printing is not performed, the enclosure (21) is covered by the gate (22) located on a linear slide and pushed by the spring (23). As the carriage (18) moves under the enclosure, it pushes the gate (22) away from the enclosure (21), thus exposing the upper surface of the laminated part to the laser beam (7).

If the scanner (28) is of the type that scans along a single line, then the carriage (18) continues its movement during the printing step so that the whole surface of the powder layer can be covered with scan lines. On the other hand, if the scanner (28) is capable of steering the beam (7) around the surface, then the platform (2) can be stationary during the printing step. The distance between the scanner (28) and the platform (2) is kept constant from cycle to cycle by downward movements of the vertical stage as the new layers are added to the laminated part. After the completion of the scanning, the carriage (18) is returned into its initial position and a new cycle begins.

A modified version of the preferred embodiment is shown on the FIGS. 19 through 23. This apparatus (FIG. 19) includes a ribbon (50) with a flat upper surface. The ribbon (50) is attached to the upper edge of the enclosure (17). The material deposition container (12) is located above the ribbon (50), so that the material has the ability to flow from the container (12) into the enclosure (17) only when the exit from the container (12) and entrance to the enclosure (17) overlap. Otherwise the upper surface of the ribbon (50), which is located in the same plane with the exit from the container and the entrance to the enclosure, blocks material flow.

In order to deposit flowable material onto the laminations carrying platform and simultaneously level the flowable material (FIG. 22), the laminations carrying platform surrounded by the vertical support structure (17) is moved under the material container (12). The material flows from the container (12) onto the surface of the upper lamination surrounded by the structure. When it moves, the lower edge (54) of the container levels the layer (53) to the desired thickness. The container (12) can have walls which are essentially vertical or form a less than 20° angle with the vertical direction.

The same method of deposition can be utilized in a version of the system which uses a rotary table as a mover of the support structure (17) instead of linear slides. In that case, the upper surface of the table serves the same purpose in the material deposition process as the ribbon (50).

After the layer has been formed, the carriage (FIG. 20) directed by linear ways (31) is moved under a flat piece (51) which is located at the compressing station of the apparatus (FIG. 21). The vertical stage (16) is elevated and the powder on it is compressed against that flat piece. The pressure of the compression is monitored by a force gage located within the support structure of the support piece. Next, the stage is lowered to establish a focal distance between the upper layer of the laminations and the laser scanner (28). The carriage is moved under the laser scanner (FIG. 23) where the laser beam directed by the scanner performs the lamination forming operation.

Besides the just described preferred embodiment, there are other possible configurations of the LOM system. All of these configurations perform the basic steps of the LOM process in different ways. FIG. 10 shows a rotary table (39) which moves the enclosure (17) containing the vertical stage (16) and the powder carrying platform (2) around a circular trajectory. The powder container/deposition device (12), the compression roller (3), and the printing scanner (28) are located around this circle and perform the basic steps of the process as the platform is transported by the rotary table (39) to them.

FIG. 11 shows a system where the powder container (12) and the roller (3) reciprocally move over the surface of the laminated part (14), which does not move in the horizontal plane. The powder is deposited from the container (12) on one or the other side of the roller (3) depending on the direction of its movement.

The deposition is accomplished by opening one of the gates (11) located on both sides of the roller. As the powder container moves away from the surface of the laminate, the printing device (28) located above it prints the cross-section slice. After that, the powder platform is lowered to accommodate a new cross-section slice.

FIG. 13 shows a roller (3) which magnetically or electrostatically attracts a thin powder layer (1) from the powder container (12) as it rotates while the powder flows onto its surface from the container (12). Simultaneously, the roller (3) rolls over the upper surface of the laminated part located on a reciprocating platform. As the roller (3) with the powder on it rolls over the surface, the powder is deposited and compressed at the same time.

FIG. 14 shows an LOM system in which a stream of particles (43), suspended in air or a cover gas, is recirculating through a loop. Part of this loop is a rectangular channel with a transparent upper surface (37) located above the top surface of the laminated part. The beam of the printing device can be transmitted through this surface. The powder deposition is accomplished by a vertical movement of the powder carrying platform (2). The powder from the stream gets caught between the upper surface of the laminate and the transparent piece (37). It is compressed by the same movement. After that, the beam transmitted through the transparent piece (37) prints the cross-sectional slice. Next the platform is lowered, allowing the steam of the suspended powder to resume its flow. The concentration of the powder in the steam is maintained by adding it from the container (12).

FIG. 15 shows a similar arrangement to the one described previously but the circulating powder is deposited and simultaneously compressed by a reciprocating roller (3). The roller (3) catches some of the powder under it as it rolls over the surface of the laminate. The printing beam (7) shining through the transparent roof of the enclosure and the semitransparent steam of suspended powder prints the slice shape on the surface of the laminate.

FIG. 16 shows a version of the LOM system, which instead of previously described cycling procedures, preforms the depositing, compressing and printing steps of the LOM process continuously and simultaneously. In this system the powder carrying platform (2) is circular. As in the rotary table version, the powder container (12), the roller (3), and the printing device (28) are located around a circle, but in this case, the powder continuously flows from the powder container (12) on the flat side of the cylindrical laminate. It is simultaneously compressed by roller (3) located along one of its radii. The scanner (28) also operates continuously along one of the radii. The platform (2) is continuously lowered as the thickness of the laminate spirally increases.

FIG. 17 shows another version of the LOM system operating in a continuous fashion, but in this case, the powder is deposited onto a cylindrical surface. The deposition is accomplished by first depositing the powder on a continuously moving conveyor belt. A cylinder (49) capable of vertical and rotary movement presses against the surface of the powder carrying belt as shown in the Figure. As the new layers of the powder adhere to the surface of the powder cylinder (14) its diameter increases. At the same time the scanner (28) prints the object on the surface of the cylindrically compressed powder layer using cylindrical coordinate system for definition of the part's geometry.

FIG. 18 shows a version of the LOM system that uses a plate conveyor (46) as an intermediate carrier of the deposited powder. First, a powder layer is deposited onto a transparent plate (37) carried by the conveyor. Then the conveyor transports the plate under the powder carrying platform (2). Next, the linear stage 16 moves the platform down so that the upper surface of the laminate presses against the newly deposited powder layer thus accomplishing the deposition and the compression. After that, the printing beam shines through the transparent plate and prints the cross-section slice. Instead of the conveyor belt, a rotary table with a transparent surface can be used as an intermediate carrier of the deposited powder. Another possibility is to have non-transparent plates on the conveyor and move them after each compression step so the printing beam (7) will go through the space between two neighboring plates.

As it was mentioned earlier, the sheet system can be constructed using many design features of the powder apparatus. In fact the same system can be used for sheet or powder processes. The preferred embodiment of this system (FIG. 24) includes the flowable substance container (12) associated with the reciprocating carriage connected to the piston-like enclosure (17) attached at the upper edge to the ribbon (50), just like it was done in the powder system shown on FIGS. 19 through 23. Additional elements of this system are a sheet feeder (57) capable of feeding sheets (60) one at a time on the surface of the ribbon (50), a vacuum pick up plate (56) capable of picking up sheets or portions of them from the surface of the ribbon or from the laminated stack. Other elements of the system are extra material remover (59), a compression plate (37) made out of material transparent to the curing energy delivered by the source (55), and a water or glue application roller (58).

There are four stations at which the process is performed. The first is the flowable material depositions station. When the enclosure (17) is moving under the material container (12), the material, which could be a powder based substance or a curable liquid, is deposited in the space bounded by one or several formed laminations and is leveled by the lower edge of the container (12) at the same time. The top surface of the laminated stack coincides with that edge when the leveling takes place. The second station is the curing or compression station. If the flowable material is a powder based material, then compression is performed by elevating the vertical stage (16) and pressing the stack against the plate (37). If a curable liquid is used, then the energy source (55) delivers the curing energy to the liquid in that position. The third station is the stacking station. At this station, a formed lamination is deposited on the surface of stack located on the platform (2). The deposition is performed by the vertical movement of the stage (16) and pressing the upper surface of the stack against the formed and adhesive coated lamination (60). At this point the suction force exerted by the suction pick up plate (56) is released. The fourth station is the sheet deposition and forming station. At this station, sheets are deposited from the sheet feeder (57) onto the surface of the ribbon (50) or a vacuum platform attached to it. The combination of the laser (29) and the scanner (28) cut the sheet on the platform to form the lamination.

The laminating cycle for the above system could be performed in the following manner. First, a sheet (60) is deposited from the sheet feeder (57) at the sheet depositing station while the carriage (17) is located in position III (FIG. 24). It is formed into a lamination by the laser scanner (28) according to the instructions of the computer. Next, the carriage (17) is moved to position II and the formed lamination is moved to position III. The pick up plate (56) picks up the lamination (60). The carriage (17) then is moved to position III. While it moves, the roller (58) activates the adhesive on the bottom of the sheet held by the pick up plate (56) or deposits a layer of adhesive. At that position, linear stage (16) moves up and presses the upper layer of laminate against the lamination held by the plate (56) causing its attachment. If there is extra material remaining on the pick up plate (56), then the carriage moves to position II. The extra material is dropped onto the ribbon (50) and when it is moved to position IV, it is pushed from the ribbon (50) by the actuator (59).

If the system is instructed to fill the space between the laminations with a flowable material, then the movement under the material container (12) is performed by the carriage (17) the same way as it was described earlier for the powder system. If the flowable material needs to be cured by the curing radiation, then the carriage is stopped at position II.

Figure 41:
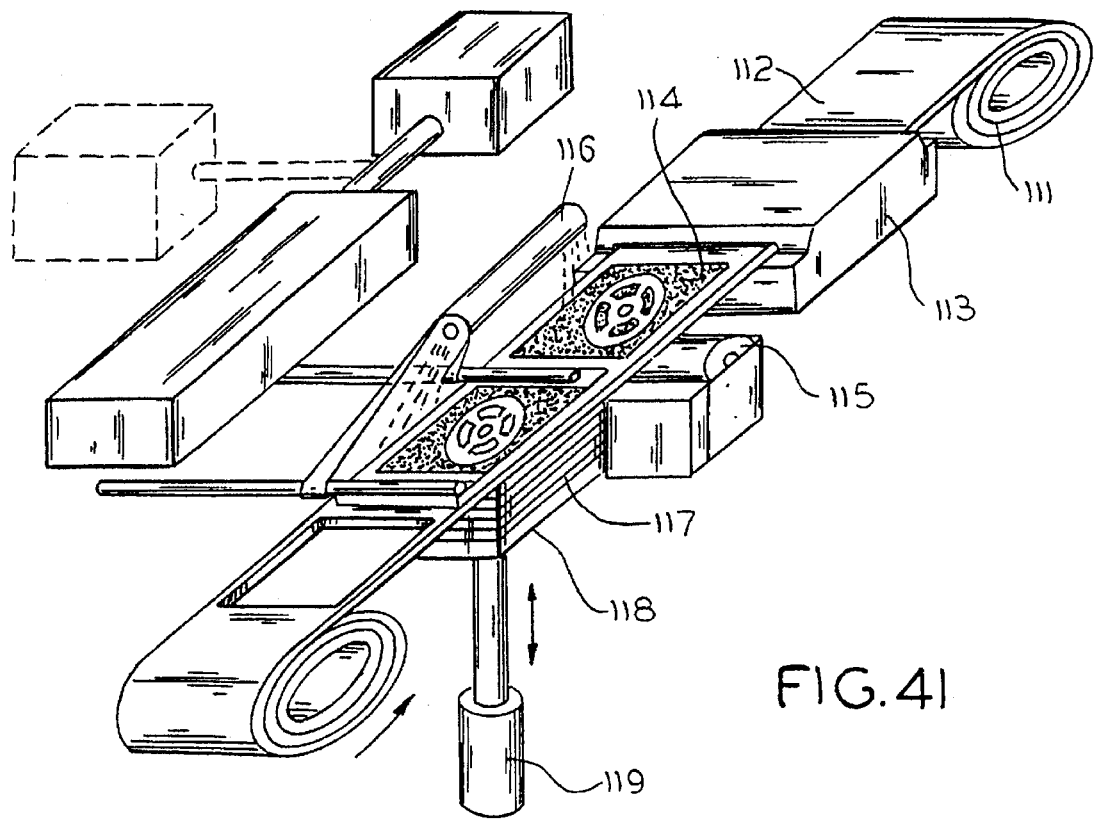
FIG. 41 is a perspective view of a cut-on-the stack sheet LOM system during the bonding step of the laminating procedure.
Figure 42:
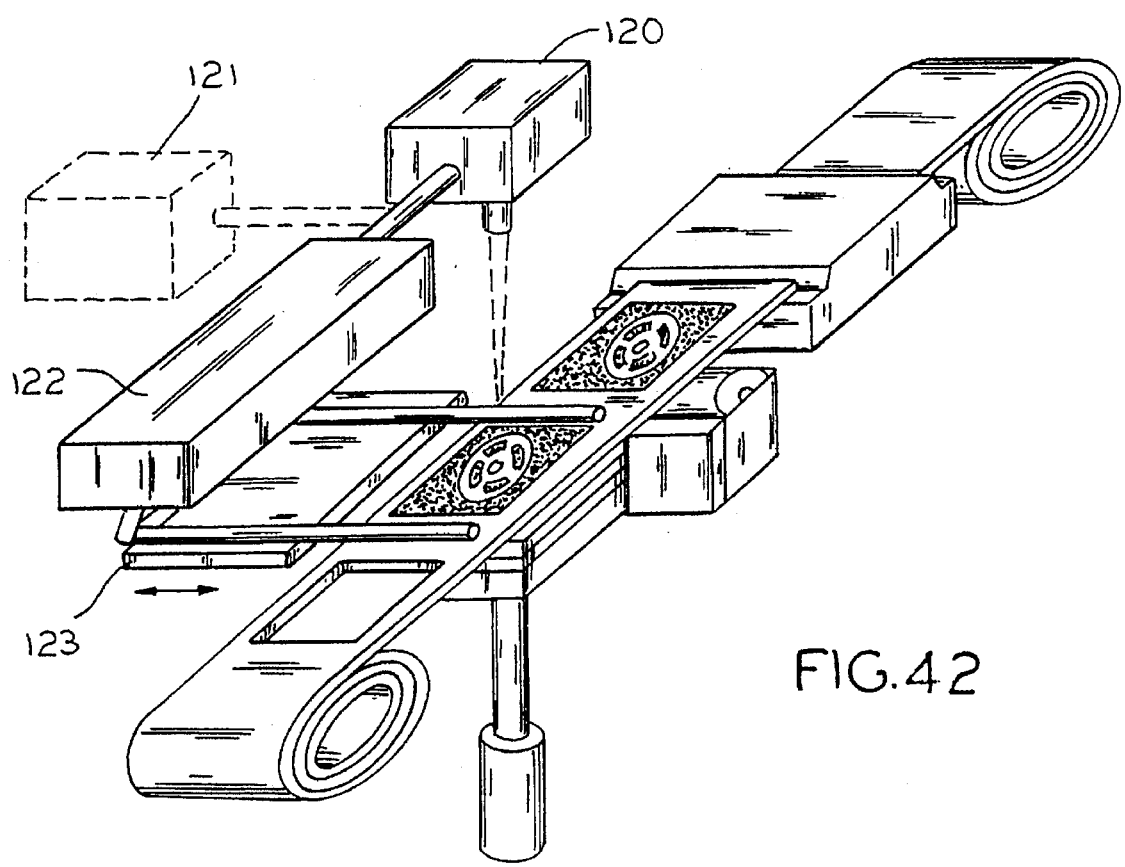
FIG. 42 is a perspective view of a cut-on-the stack sheet LOM system during the cutting step of the laminating procedure.

Another preferred embodiment of the sheet LOM system is shown in FIGS. 41 and 42. This system includes a $CO_2$ or YAG cutting laser (122) and beam positioning device (120), which might be a scanner or an XY table. Platform (118), capable of computer controlled movement towards and away from the scanner, is positioned under the scanner (120) by a vertical stage (119). The upper surface of the platform (118) is used for carrying laminations. Above the platform there is a ribbon handling mechanism capable of computer controlled handling of the sheet material (112) fed from a roll (111). This material can be also fed on the top of the laminated stack from a sheet feeding mechanism.

The material could be a plastic film, paper, B-staged fiber reinforced composite, foil or any other sheet material that can be cut by a laser beam (7). As the ribbon of sheet material (112) is positioned above the laminated stack (117), if needed, it is coated with a glue from a glue depositing mechanism (115). After application of the glue, if any, the ribbon (112) is pressed against the stack (117). Heat activated glue or bonding agent could be present on the roll (111) while tacky adhesive could also be present if a release layer was included in the roll (111) and stripped off before stacking. To achieve a uniform bond, a roller or a flat plate (123) is used for applying pressure against the ribbon (112).

After the sheet has been attached to the stack, the laser beam (7) forms a cross-section slice by cutting the material on the top of the stack preferably to the depth of one lamination. The system can be built to selectively bond portions of material, which belong to the laminated object, onto the stack. For example, if a heat activated glue is used in the process, the same laser (122) that performs the cutting could be used to selectively heat the material of a cross-section in order to bond needed portions of it to the stack before the cutting (just move the beam faster or defocus it). Typical materials include paper coated with a thermoplastic or thermoset, polyester coated with an adhesive on one or both sides, woven and nonwoven fiberglass, Kevlar, or carbon fiber coated with a thermoplastic, or ceramic tapes impregnated with a thermoplastic binder, bimaterial composites, and composite tapes impregnated with a thermoplastic or other binder. Objects directly obtained from tapes may subsequently fired in a furnace to reduce thermoplastic content. If green ceramic tapes are used in the process, an organic or an inorganic mesh material of greater strength is preferred to support the ceramic, which normally is very fragile. An additional UV laser (121) can be added to the system (possibly using the same scanner (120)) in order to selectively activate the adhesive within the boundary of a lamination.

Another way to achieve a selective bonding is to use a printer (113) for printing negatives of slices on a ribbon (112) that is transparent before placing the material on the stack. The picture obtained in this manner will serve as a mask for selecting areas of a slice to be bonded to the stack. The bonding can be accomplished by pressing the material (112) with the mask printed on it against a flat piece of glass (123) and exposing the material to a UV light from a lamp (116). After the bonding, the glass and the lamp are moved aside and the laser beam (7) performs the cutting to the depth of one lamination. The precision of positioning of the printed cross-section on the stack is not a serious concern since the final precision of the part will be determined by the cutting laser beam, just like is done in the sheet feeder version of the machine. The masking images created on the laminated sheet can be printed in color and extend a short distance inside the boundaries of the cross-sections which they represent. The coloring of a lamination should correspond to the color of the three-dimensional surface of the computer generated image at the level of that particular lamination.

A wire screen made out of very thin (0.001–0.005") wires forming a grid with fairly large (0.020" or larger) cells could be substituted for the glass plate (123). Since the wires have a diameter that is only a small fraction of the normal spot size of 0.010", they allow the laser beam with the spot size 0.010" or larger to process the material underneath with minimal diffusion. A negative air pressure applied from the top of the screen could attract the unneeded material surrounding slices that have been bonded to the stack using selective bonding techniques described earlier and to remove any smoke that might otherwise obscure the laser beam (7). In case of metal foils containing magnetic material, this operation could be performed using electromagnetic force applied in a similar fashion through a non-magnetic screen or thin glass. Extra material will be moved with the screen away from the stack and discarded in a waste basket as the negative air pressure or the electromagnetic force is eliminated.

Using these techniques, three-dimensional objects can be manufactured out of more than one material by either supplying different materials for different laminations or even by supplying different materials for a single lamination. The materials that comprise a single lamination can be attached to the adjacent lamination by sequentially performing a previously described selective bonding step for each of them, followed by the lamination forming step outlining the area comprised of this material, following by the removal of the material surrounding that portion of the lamination.

Figure 35:
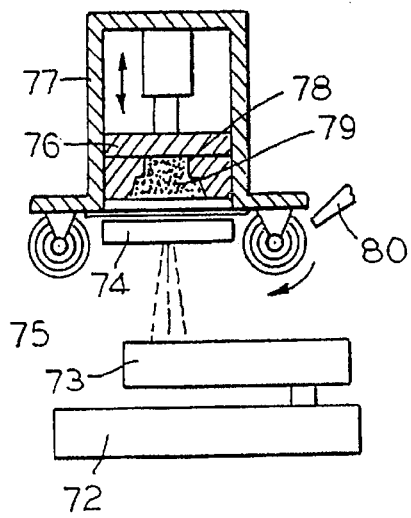
FIG. 35 is a cross-sectional view of a cut-on-the-stack sheet LOM system capable of selectively attaching cross-sectional layers of a part to the laminated stack and automated removal of cut off material.

Another version of the cut-on-the-stack machine, which has the capability of removing the extra material surrounding each cross-section during each laminating cycle, is illustrated on the FIG. 35. When a metal part is being constructed, a metal cutting YAG laser (72) generates a laser beam (7) that is manipulated by a beam positioning device (73). This device may be a scanner or an XY table carrying two reflecting mirrors or an optical fiber transmitting the beam. A metal ribbon coated on the top with a thin layer of copper is fed from a roll (75). If the ribbon is not clad with copper, a thin layer of brazing paste or a glue can be deposited from a depositing device (80) as the ribbon is cycled back and forth.

Initially, the stacking platform (76) moving within the cylinder (77) presses the ribbon against a flat piece of glass (74). Next, the laser beam brazes the first cross-section slice to the platform (76) by performing a relatively fast movement within the slice. A possible trajectory of this movement for a newly attached cross-section slice is a line parallel to the periphery of the slice preceding it on the stack and located within it. Later, the platform (76) moves a short distance away from the glass and the laser performs cutting in the high power pulsing mode. The power of the beam is adjusted to perform cutting to the depth of a single lamination. A rectangular periphery is cut around the cross-section slice. This releases the ribbon for further movement. The cut off pieces fall onto the glass (74). They are swept by means such as a reciprocally moving wiper blade into a waste basket. The ribbon (75) advances and the process resumes. After all of the laminations have been deposited and cut, the part (79) is removed from the platform (76).

If a plastic film is used for the production and a $CO_2$ laser is required instead of a YAG one, then a wire screen having wires, which are thinner than the laser beam that passes through the mesh, can be substituted for the glass (74). If a UV curable adhesive is used in the process, then a UV laser can be associated with the $CO_2$ laser in a manner similar to that described for the previous versions of the system.

Figure 43:
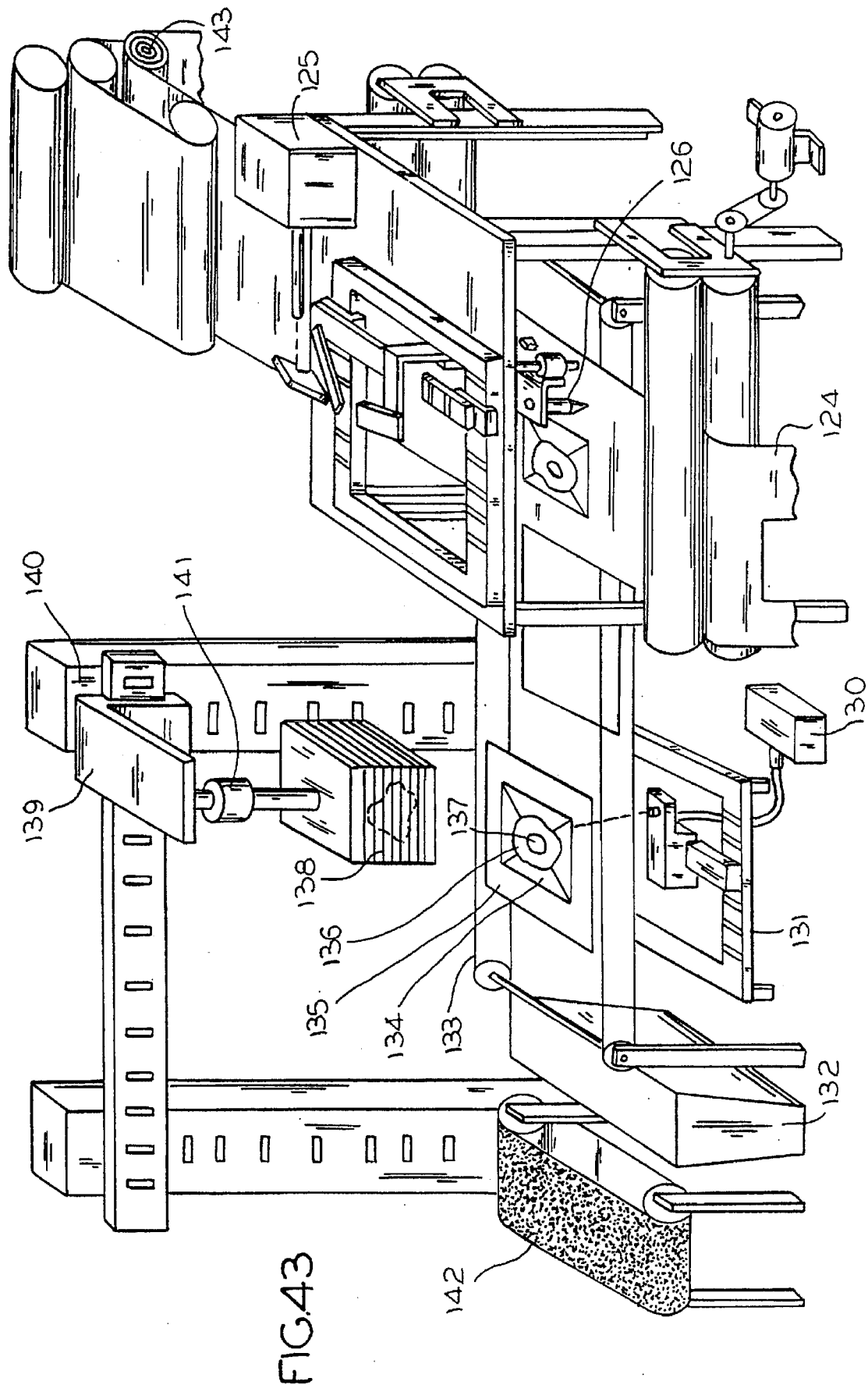
FIG. 43 is a perspective view of a cut-off-the stack LOM system.

A cut-off-the-stack version of the system is illustrated on the FIG. 43. This type of a system can be used for the production of plastic and metal parts. In case of producing a part out of metal, a sheet metal ribbon is fed into the machine from a roll (143). The ribbon (124) is made from 0.002"–0.015" thick metal clad with a material of lower melting temperature (e.g., copper) on the top. Just like in the previously described version, a brazing material depositor may be incorporated into the system to avoid the necessity of using a clad or coated material. Copper is known to reflect laser beams. However, the inventor's early experiments have shown that its thickness is not sufficient to significantly impede the cutting process. Successful samples have been produced even when cutting from the copper coated side. A laser beam is generated by the laser (125) and directed to a cutting area of the ribbon (124) either by two mirrors (127) and (129) attached to X and Y stages of the positioning table (128), or a scanner. The beam is focused on the ribbon (124) with a focusing lens located on the Z stage (126) of the positioning system.

The laser (125) must be precisely located with respect to the mirrors (127) and (129), but commercially available lasers are not precisely aligned with their cases. Therefore, a mounting plate is precisely aligned with the laser beam the laser produces at the factory to make the lasers interchangeable. Thereafter, field replacement of lasers becomes easy, requiring no field alignment.

In the process of creating a laminated part, the laser beam is manipulated with the XYZ positioning table to cut a cross-section slice of a part designed on a CAD system. A five axis laser system can be utilized at this stage, to achieve a better approximation of the final geometry of the part by tilting the laser beam during the cutting step to bevel the edges of the slice. Initially a rectangular sheet larger than any cross-section slice is cut out of the ribbon. It drops onto the conveyor (133). The conveyor carries several glass plates (135) transparent to the YAG laser beam. As the rectangular portion drops, it may be attracted to the surface of the plate by a magnet positioned under the plate (if it consists of a magnetizable material). After cutting the rectangular boundary the laser beam cuts the rest of the cross-section around its periphery as it rests on the conveyor. Preferably, the material of the conveyor is minimally absorbing and maximally diffusing of the laser radiation used for cutting.

Later, the conveyor (133) moves the cut slice to the stacking station (140). After the slice (134) is positioned under the stacking platform (139), the platform is moved downward until the stack located on it presses against the slice (134) to be attached. A load cell (141) produces a load feedback signal so that the platform pressure can be controlled. The amount of load necessary to apply proper pressure to a particular rectangular portion is proportional to its area. The area and hence the proper load is calculated by the computer.

Once the cross-section slice is pressed against the stack, the second laser (130) turns on. Its beam is manipulated by a second XYZ positioning system (131) or by a scanner to scan the bottom surface of the cross-section slice within the area to be attached to the stack, such as portion (136). If parting lines have been cut in the material surrounding a cross-section slice, as shown in the cross-portion (134), the beam can raster scan the whole rectangular area and the surrounding material can be separated from the part in a mold like fashion. Otherwise, the extra material surrounding the newly attached cross-section slice stays on the conveyor as the laminating platform (139) is elevated. This material gets discarded into the waste basket (132) as the conveyor moves for a new cycle. The intensity and the speed of motion of the beam from the second laser (130) has to be adjusted to melt the brazing layer. Instead of having a second laser, the beam from the laser (125) can be split into two beams, with the second beam utilized for brazing.

In order to achieve successful lamination, the bottom of the stack should be free of oxide film and of dross (resolidified metal drops which are usually produced as a result of laser cutting). To clean the bottom of the stack, the positioning system of the stacking station (138) brings it into the contact with a grinding belt (142).

Figure 44A:
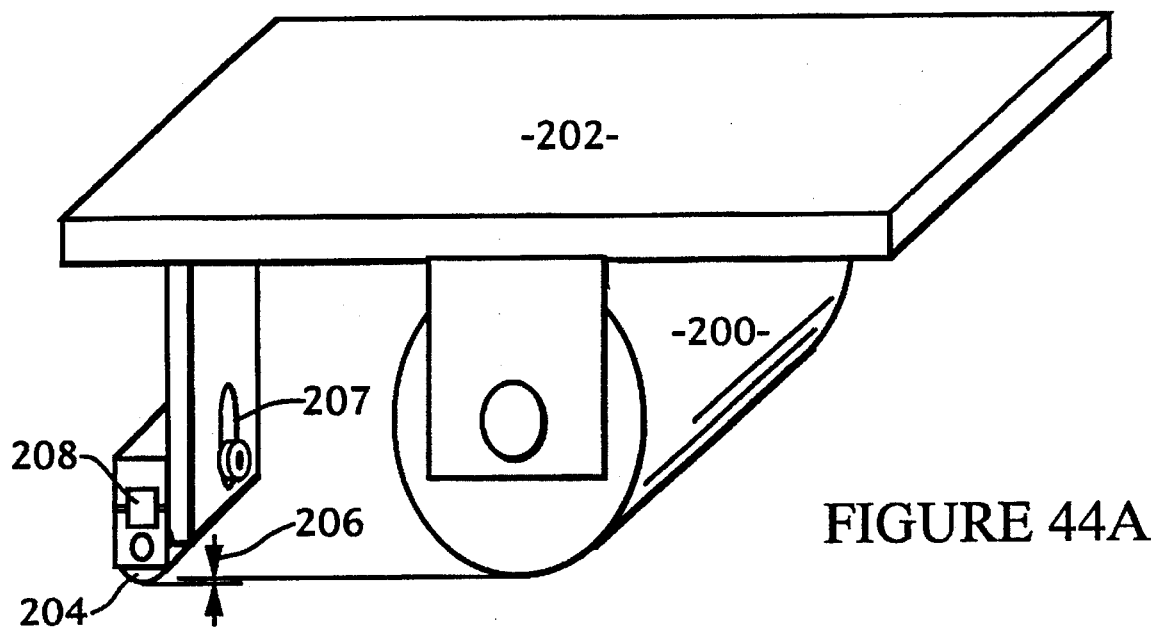
FIGS. 44A and 44B are detail views of a heated bonding roller with a force sensor, and the interference between the heated roller and the stack.
Figure 44B:
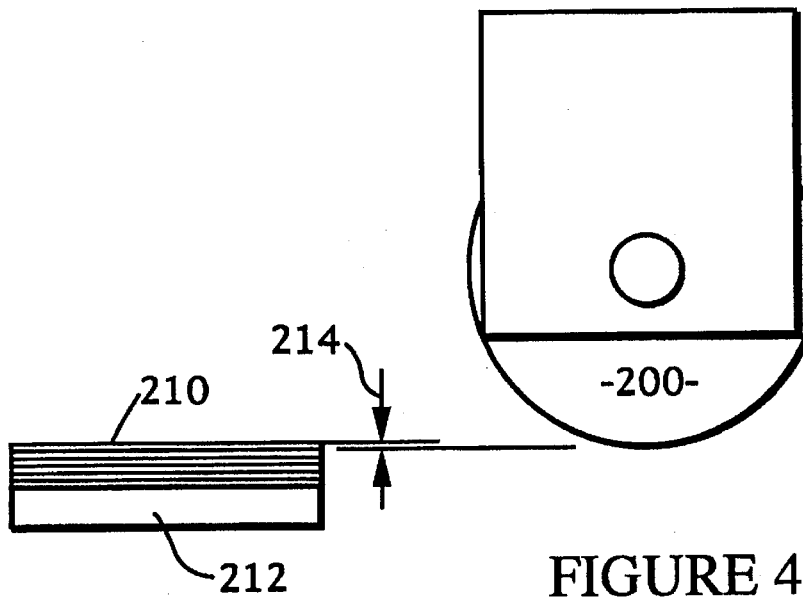
Figure 44C:
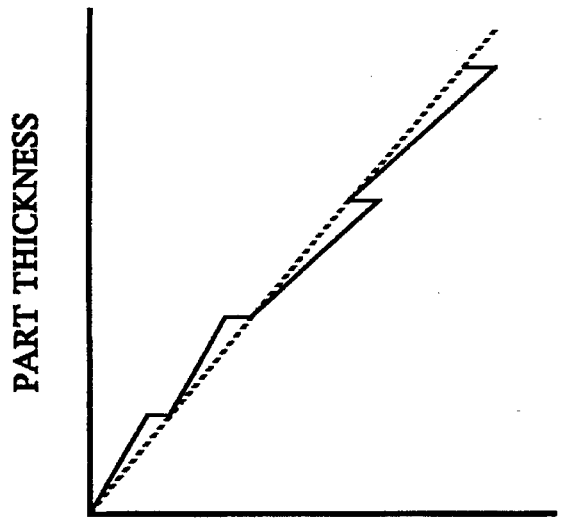
FIGS. 44C and 44D are graphs of part thickness versus number of layers for two different correction methods possible when a height or force sensor is used.
Figure 44D:
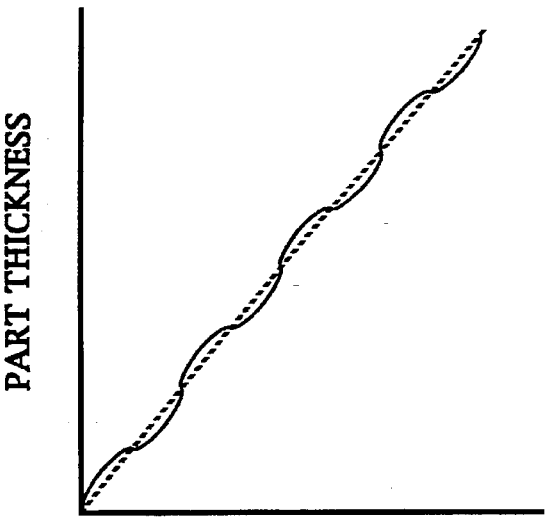

Laminate material has different thickness tolerances from run to run or within a run. Therefore, it is desirable to form the cross-section slices of an object in response to the thickness of the material being used for the lamination. FIG. 44A shows the detail of a modified heated bonding roller (200) whose frame (202) rigidly supports a sensor roller (204) that extends below the roller (200) by a predetermined amount (206) that is adjustable in the slot (207). Sensors (208) measure the deflection of the sensor roller (204) and this information along with platform position is provided to the computer, which divides the number of laminations on the platform by the measured distance, thereby calculating an average thickness for the laminations on the platform. Using this number, the computer then calculates the next cross-sectional slice. By performing the calculation as an average of the laminations present, rather than trying to measure the thickness of the last lamination, corrections can be made without danger of a loss of stability that might occur should the sensor (208) be noisy or the roller (204) acquire a gob of adhesive on its surface to occasionally produce erroneous measurements. After the height of a stack of laminations (210) has been sensed, the platform (212) can be adjusted to establish the desired interference (214) between the heated roller (200) and the stack (210) to assure proper bonding pressure. FIGS. 44C and 44D are graphs comparing a method of arriving at the computational thickness for consecutive layers of the object produced by the LOM machine based on the direct results of the measurement by the total accumulations sensor (208) (FIG. 44C) versus gradual adjustment (FIG. 44D) of the computational height based on statistical averaging of the thickness of the accumulated layers. The correct part thicknesses versus the number of layers are shown by the dashed lines.

When the shape of each slice is calculated just before it is cut, less precise sheet material can be used. Such calculation time also enables the computer to work in parallel with the LOM device rather than spending time calculating all of the slices while the LOM machine remains idle.

The height of a stack also can be obtained by placing force sensors in position to support the roller (200). A chosen force is then maintained by adjusting the amount of movement of the platform (212) between lamination placements. The thickness of the stack (210) need not be calculated as it can be directly obtained from the platform position with small adjustments being made from step to step based on prior sensed roller load and a correction algorithm to maintain the load within a small range, which also establishes the proper bonding force between the laminations.

Figure 45:
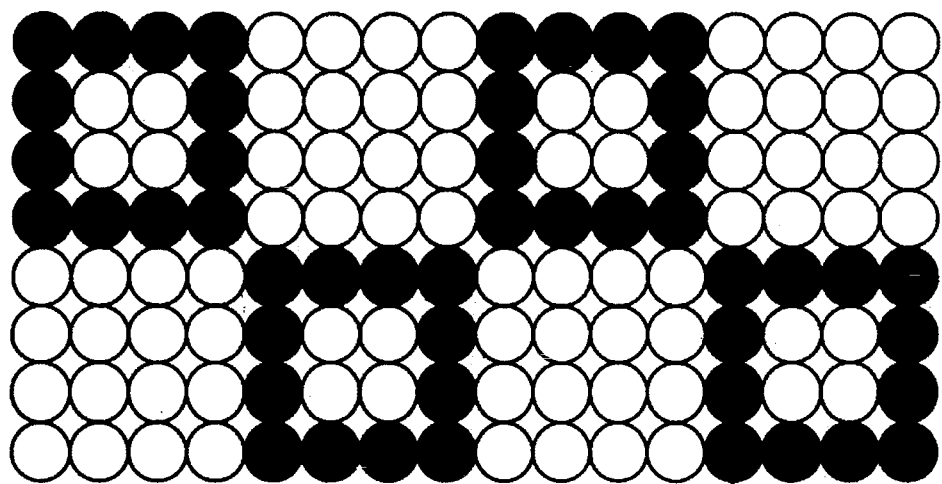
FIG. 45 is an enlarged view of a diode array.
Figure 46A:
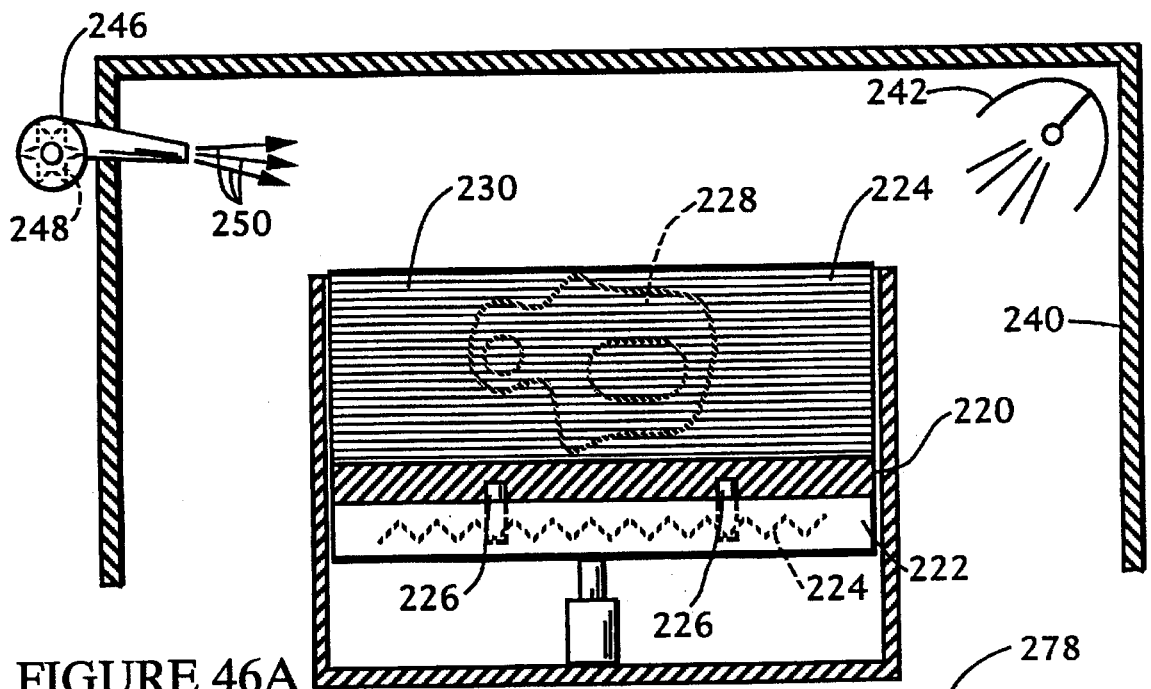
FIGS. 46A and 46B are diagrammatic elevational views of a platform with a disposable subplatform and a side view of a soft centered subplatform respectively.
Figure 47A:
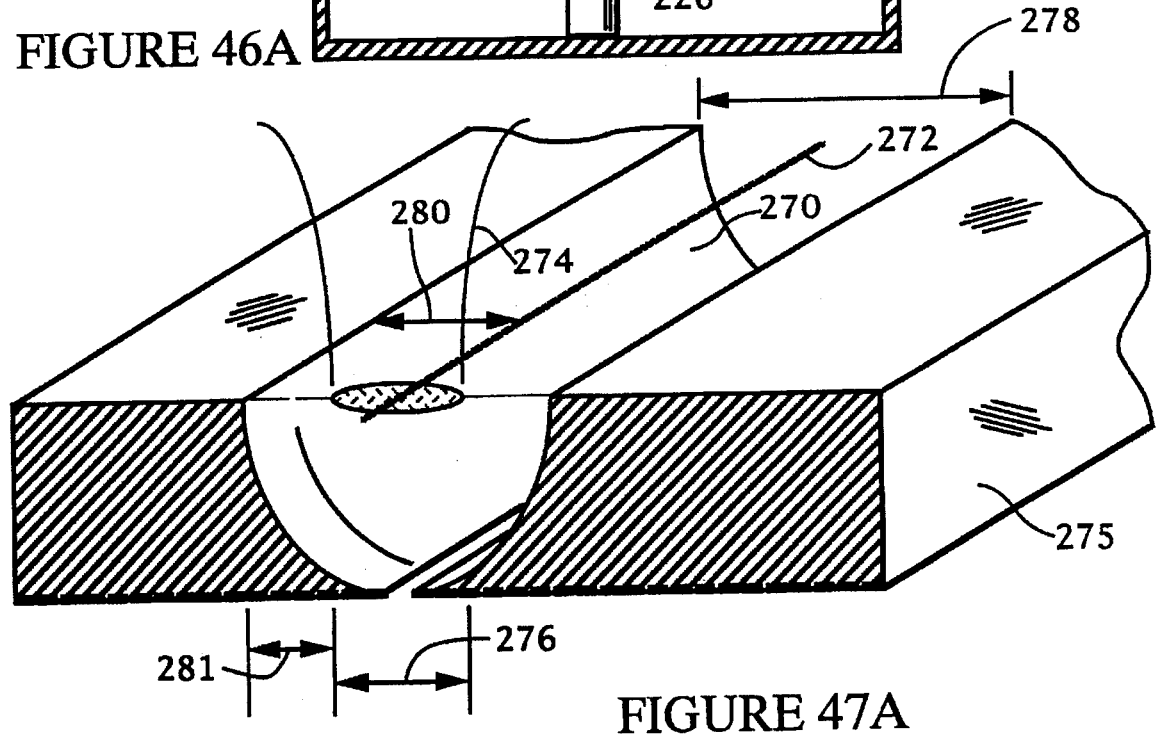
FIG. 47A is a greatly enlarged cross-section of a cut line.
Figures 46B, 47B:
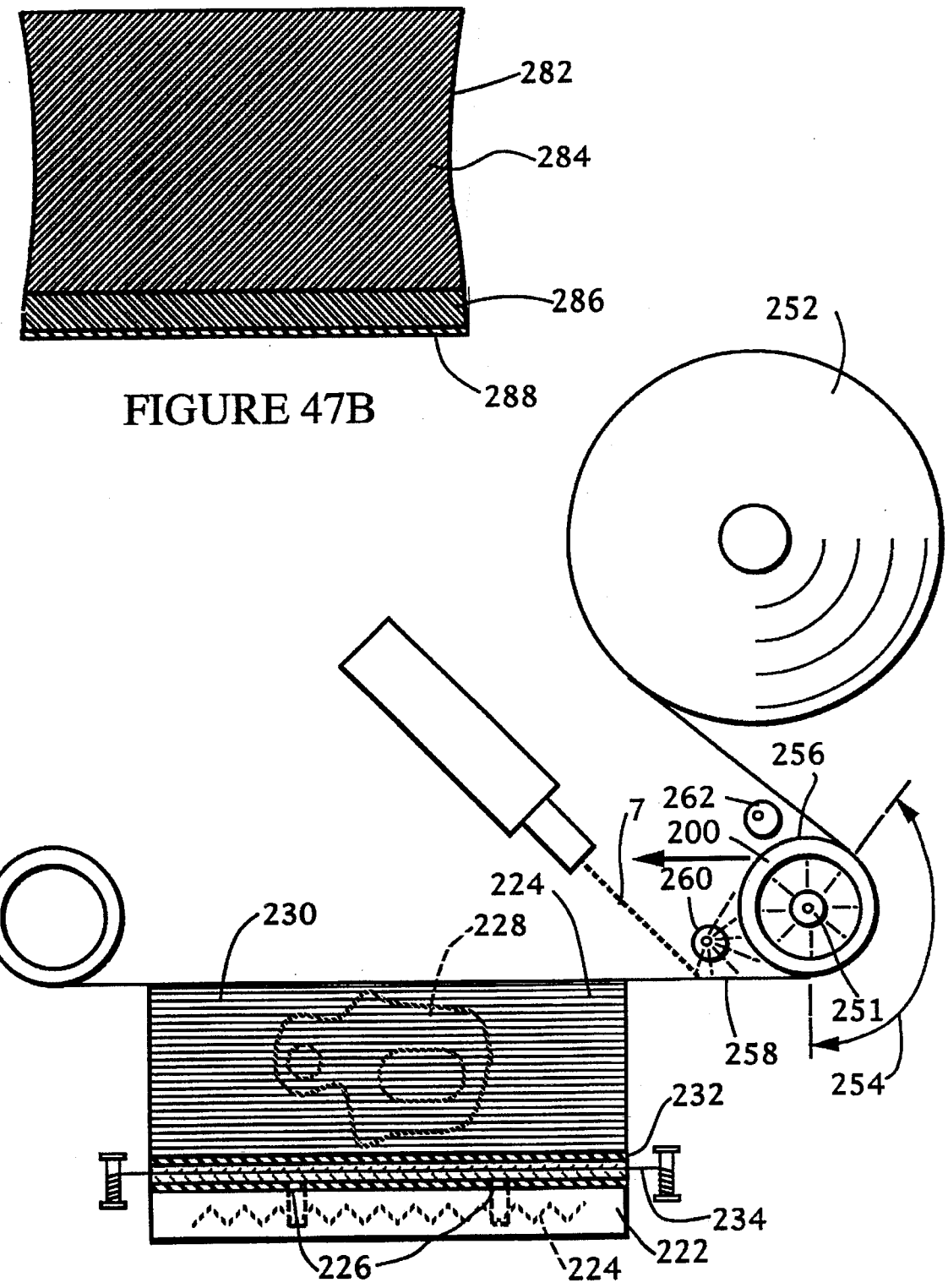
FIG. 47B is a greatly enlarged cross-sectional of a special lamination material.

A finished stack of laminations, having the object there inside can be difficult to remove from the platform (212). One method is to lay down a first lamination that is finely cross-hatched over its entire surface so that the next lamination is poorly bound thereto. Such fine cross-hatching could be created by a special multiple beam laser diode array (216) as shown in FIG. 45 usually mounted to move directly over the lamination. However, such intentional weakening can result in a partially completed stack being shoved off the platform by the bonding roller. FIG. 46A shows another solution to the stack platform separation problem wherein a disposable platform (220) is placed on the working platform (222) and then the stack (224) is bonded only to the disposable platform, it having a thickness sufficient to prevent bonding of the first lamination layer to the working platform (222). The disposable platform (220) may be retained to the working platform (222) by means such as locating pins (226) and a magnetic, vacuum, mechanical, or other type chucking device. The advantage of a disposable platform, even though it may be reusable, is that it can be quickly removed from the working platform (222) so that the next object can be constructed while the prior object (228) is being removed from the stack (224). As shown in FIG. 46B, the disposable platform (220) could have a soft center such as the foam layer (232) so that means such as a music wire guillotine (234) can quickly remove the completed stack (224) from the working platform (222).

No matter what the material used, LOB generated parts tend to have internal stresses that can cause part distortion, especially in thick parts. In order the minimize the effects of internal stress and to uniformly distribute the stresses within the part, as well as requiring less energy transfer between a heated roller to initiate bonding, a heat controlled environment may be established about the stack (224) during its formation. This can be done in numerous ways, including those shown in FIG. 46A, which include an enclosure (240) having an infrared heat lamp (242) therein and/or heater elements (244) within the working platform (222) or even a air blower (246) that includes a thermostatically controlled heater element (248) therein to provide air (250) within the enclosure (240) at the desired temperature. The blower (246) is particularly advantageous in that it also can be used to blow smoke caused by the cutting of a slice out of the path of the laser beam (7) so that the beam (7) is not distorted or diffused by the smoke, which in some circumstances could result in incomplete cutting. By keeping the stack (224) at a constant elevated temperature, thermal stresses do not build up in the stack (224) since the bonding temperature is only slightly above the bulk temperature of the stack (224). After the object (228) is completely formed within the stack (224), the temperature within the enclosure (240) is slowly lowered or the stack (224) is removed from inside the enclosure (240) and put in an annealing oven where the temperature can be lowered slowly while another object is constructed on the working platform (222). This allows material of the object (228) to uniformly cope with any dimensional changes caused by its thermal expansion coefficient so that warpage is minimized.

The bonding heat need not be applied by the roller (200) at all, but instead it can be applied directly to the lamination ahead of the roller such as by directed beams of IR energy or a fast scanning of the laser beam (7) to raise the material above its bonding temperature and in that case the roller (200) only applies the bonding pressure. The laser beam (7) can be finely aimed so as to heat only selected areas of the lamination so that bonding only occurs where needed. Such selective bonding makes removal of the finished object easier.

As shown in FIG. 46B, if heat is applied by the roller (200) such as by means of a heating element (251) included therein, it is advantageous to arrange the geometry between the supply roll (252) and the roller (200) so that a substantial wrap angle (254) of the sheet material occurs around the roller (200). This creates additional contact area, which allows the roller to operate much faster since it is not restricted by the amount of heat that can flow from a narrow line of contact across its surface (256) to the sheet (258). Switchable IR heaters (260) and (262) also can be employed adjacent the sheet (258) and roller (200) to provide additional bulk heating.

With high power lasers, it is sometimes difficult to control the depth and width of laser cuts. FIG. 47A shows a highly enlarged cut (270) about the path (272) of the laser beam (274) in sheet (275). Note that the beam width (276) is about ⅓ of the cut width (278) and that the calculated path (272) is substantially offset, arrow (280). The offset (280) can be determined in advance and its calculated path (272) moved sidewardly to compensate because it is one half the beam width (276) plus the sideward overburn distance (281).

Figure 47C:
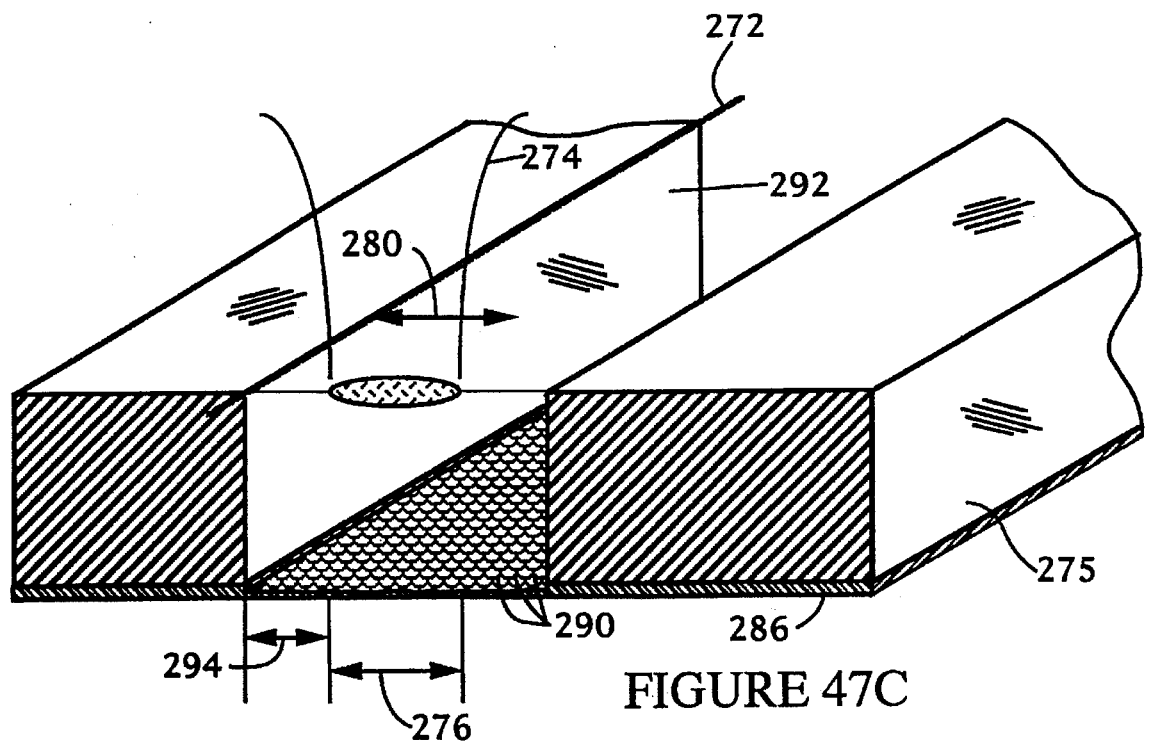
FIG. 47C is a view similar to FIG. 47A using the lamination material at FIG. 47B.

Typically, the cut (270) has curved sides as shown. If the laser energy is increased so that the cut (270) is square, then there is a danger of cutting the next lower lamination when cut-in-place is being used. A special sheet (282) is shown in cross-section FIG. 47B. In addition to sheet material (284), it includes a layer of transparent thermoplastic (286) having a metalized outer edge (288) such as by means of the imbedded metal flakes (290) shown in FIG. 47C. The metal reflects the laser beam (274) so it doesn't cut any underlaying layer. Therefore the laser energy can be increased so that the square cut (292) results. Note that the laser beam (274) has been offset by the distance (294) from the calculated cut path (272).

Figure 48:
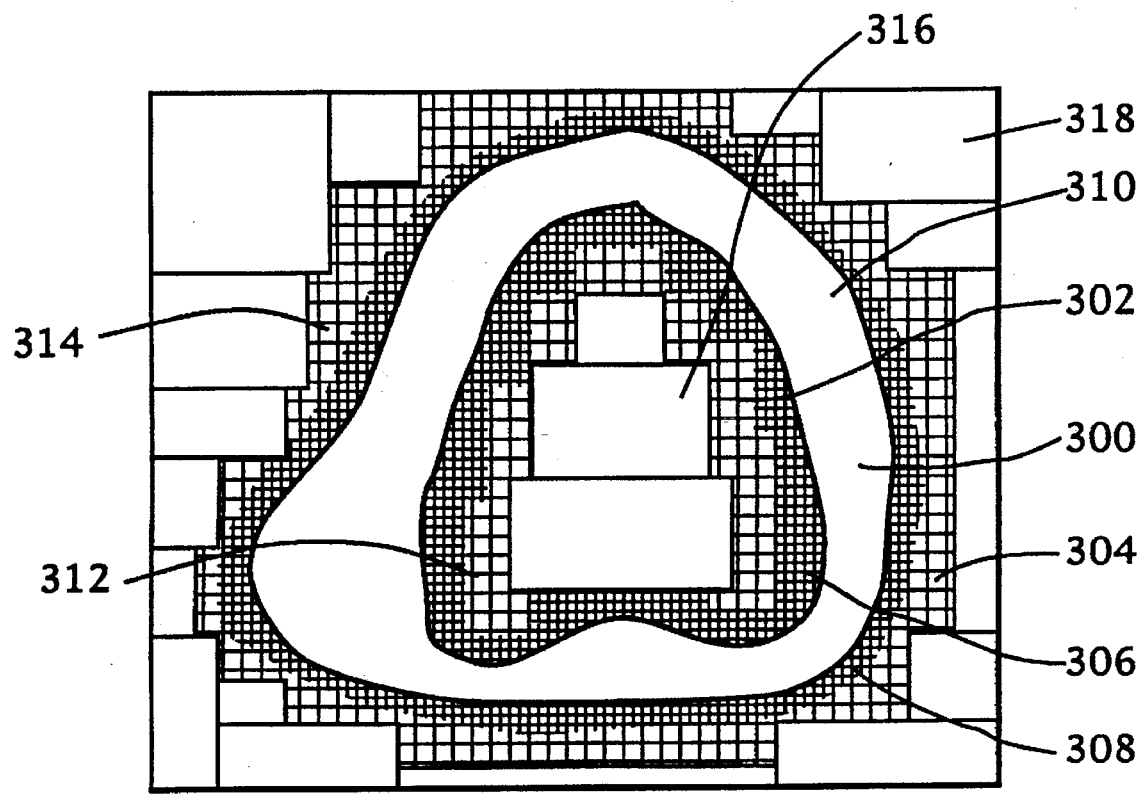
FIG. 48 is a plan view of a lamination showing variations in cross-hatching about a slice of an object so the completed object can be removed easily from its surrounding supporting structure.

FIG. 48 illustrates a lamination showing another way of easing separation between a cut-in-place object (300) and interior and exterior waste (302) and (304). As can be seen, fine cross-hatching (306) and (308) is cut adjacent the inner and outer surfaces of the slice (310) of the object. Larger cross-hatching (312) and (314) is formed adjacent the inner and outer fine cross-hatching (306) and (308) while the center (316) and the exterior (318) is cut in relatively large blocks to support the object (300) as it is being constructed. The cross-hatching can be any shape, and should be the same from lamination to lamination so that blocks or columns are formed, except for changes to accommodate the shape of the object (300).

Figure 49:
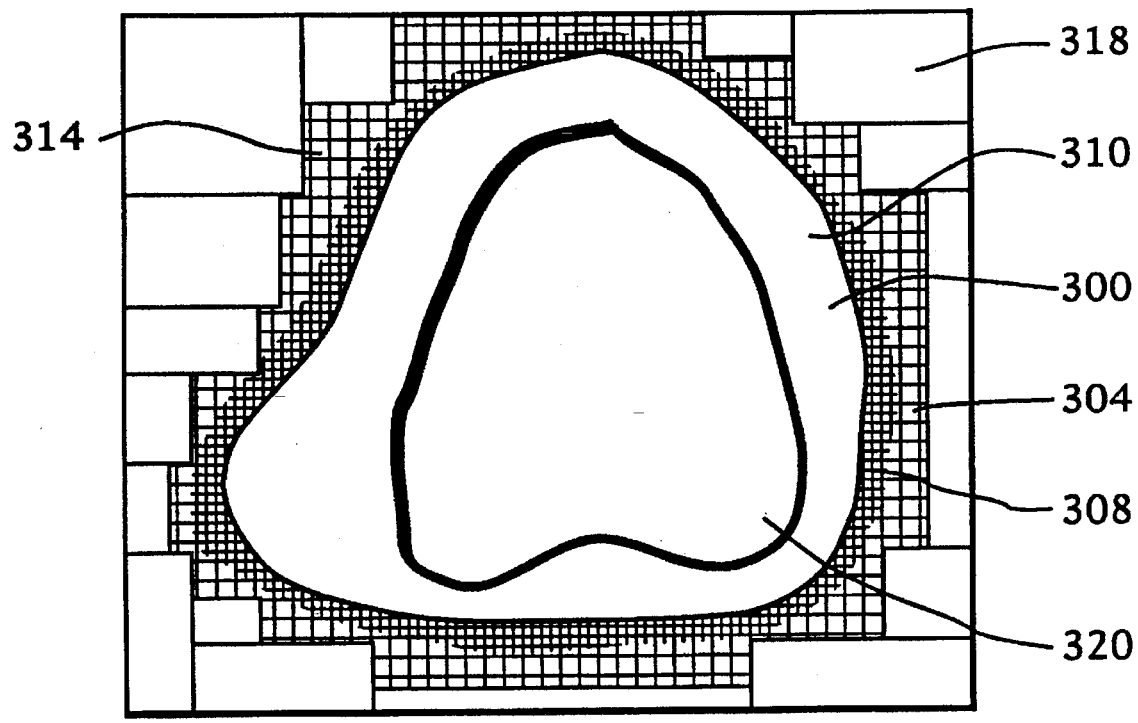
FIG. 49 is a plan view of a lamination similar to FIG. 48 wherein the center of the slice has been completely burned away.

As shown in FIG. 49, when the exterior fine, medium and block cross-hatching (308), (314) and (318) are sufficient to support the object (300) and the interior (320) of the object (300) is difficult to get to once finished, the entire interior (320) can be burned away. A preferred method of totally removing the interior is to cut the shape of the object as before and then slightly de-focus the laser beam to create a wider beam, which is then scanned over the interior (320).

Figure 50:
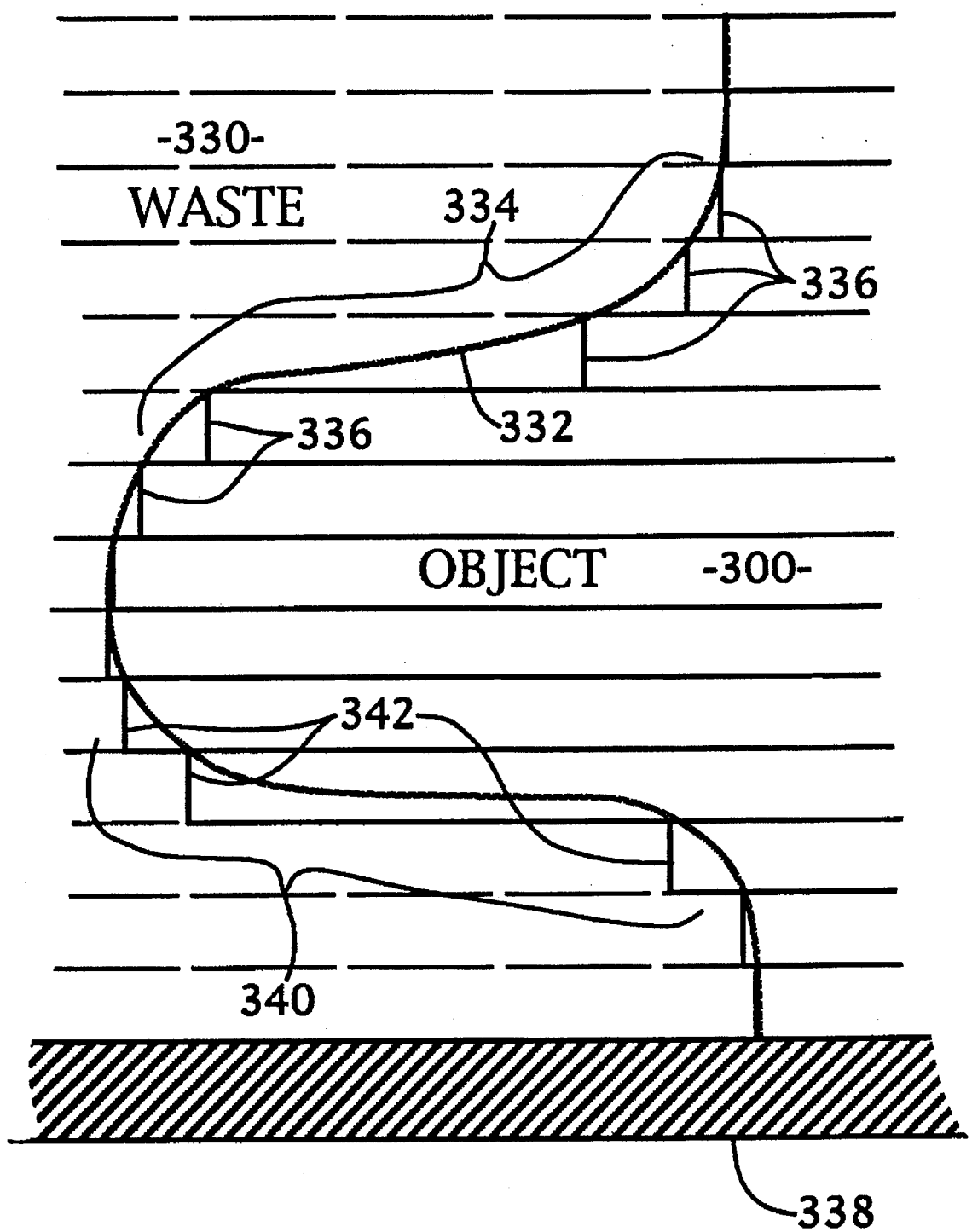
FIG. 50 is a highly enlarged, idealized elevational cross-sectional view through a stack of laminations showing the interface line between an object and the waste, wherein the shapes of the slices have been calculated based upon infinitely thin cross-sections at elevations equaling the height of each lamination of the stack.

FIG. 50 is an idealized, elevational cross-sectional view of the interface between the object (300) and the waste (330) with the calculated exact surface of the object (300) being shown by heavily dashed line (332). Note that in the area of positive slope (334), the edges (336) are cut at the intersection of the line (332) and the surface further away from the base or platform (338), resulting in an object (300) having a shape undersized from actual, whereas in the area of negative slope (340), such a cut technique results in slices having edges (342) that are beyond the calculated line (332). The cuts (344) in the area of negative slope (340) are advantageous as the extra material can be easily removed by sanding, whereas the cuts (336) resulting in an undersized object must be filled or the roughness they create ignored.

Figure 51:
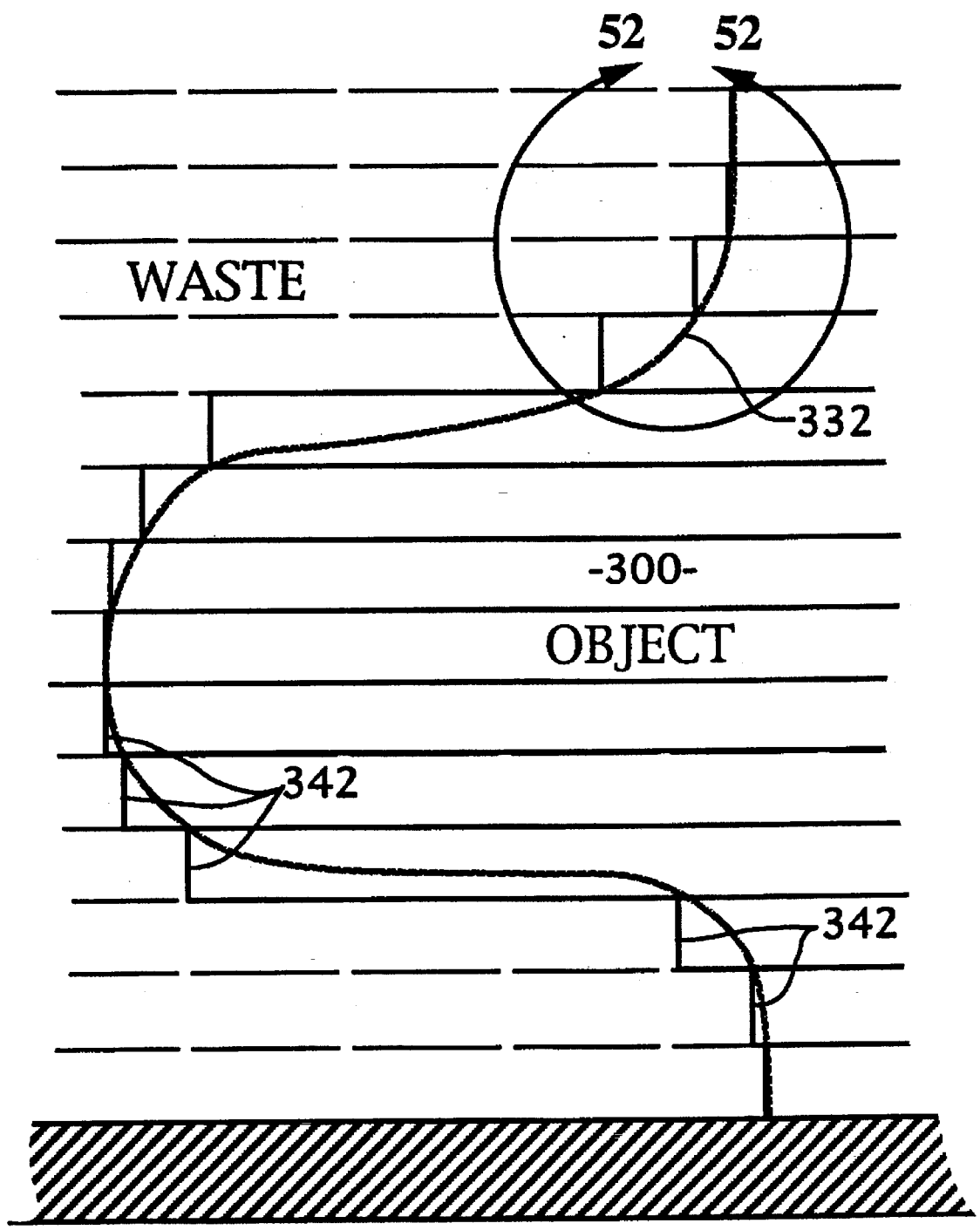
FIG. 51 is an elevational cross-sectional view similar to FIG. 50 except that the edge of each slice extends vertically from either the upper surface cross-section or the lower surface cross-section of a slice, depending on which will include more of the volume of the object.

As shown in FIG. 51, the cuts can be calculated to be at the intersection of the line (332) at whatever elevation on a slice results in the most material being part of the object (300) so that any roughness that results can be easily sanded back to the exact calculated shape line (332). Since any sanding will result in a slight reduction, it is possible, as shown in FIG. 52, that the cuts (334) be also extended by a predetermined distance (346), which allows for a slight material removal (a small fraction of 0.001" thickness of a lamination) even after the surface of the object has been smoothed so that the final resultant object has its outer surface at the line (332).

Figure 52:
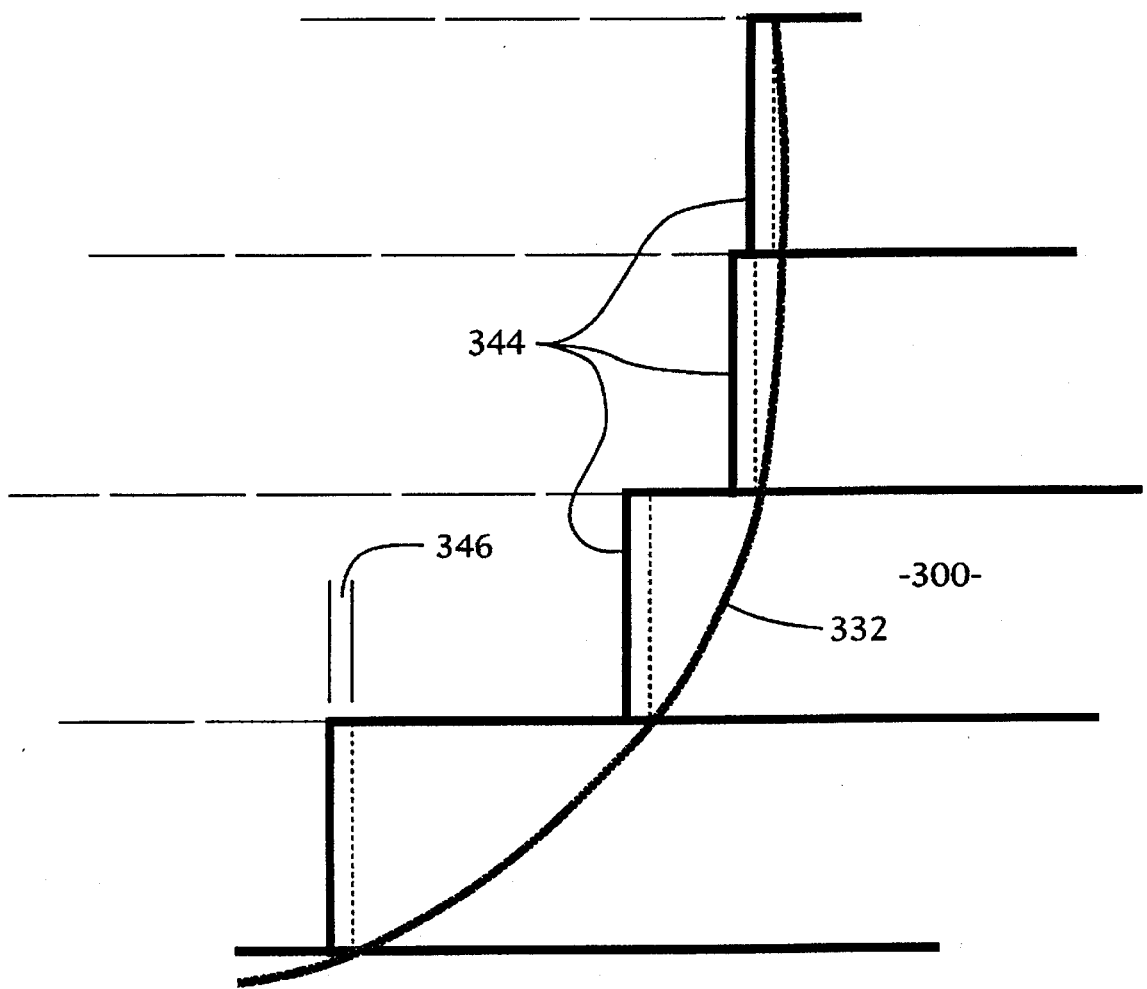
FIG. 52 is a greatly enlarged cross-sectional view of an area similar to that encircled by line 52—52 in FIG. 51 wherein the edge of each slice has been extended a predetermined amount beyond the location of the calculated object surface to provide extra material for removal during a sanding process to smooth the surface of the object.
Figure 53:
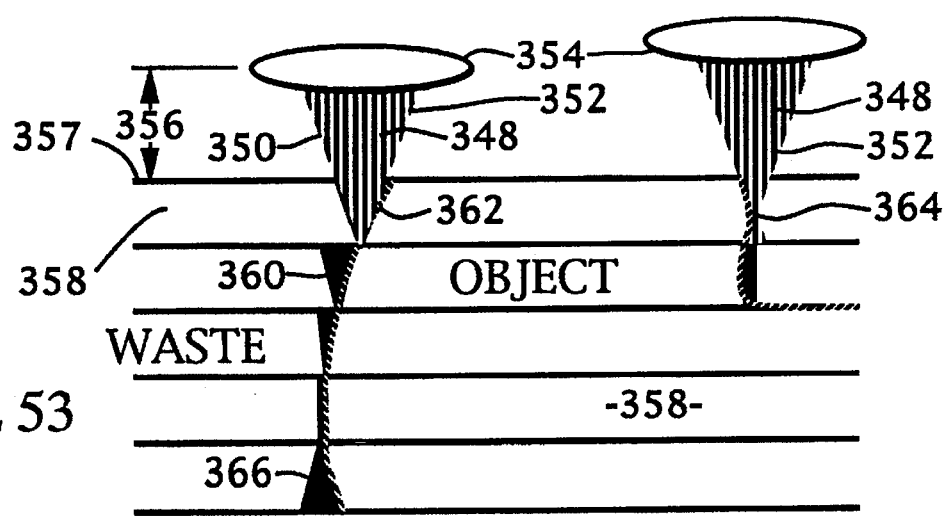
FIG. 53 is a diagrammatic elevational cross-sectional view of a stack whose slices have been cut by a laser beam having a variable beam angle and whose focus depth also can be varied.

In FIGS. 50 through 52, the assumption was made that the cutting beam was of extremely small diameter with straight sides. As shown in FIG. 53, it is possible to produce laser beams (348) having angled sides (350) and (352) by focussing the laser beam (348) through lens (354) maintained a very close distance (356) from the exposed surface (357) of the lamination (358) being cut. In the case of beam (348), its sides (350) and (352) are shown being adjustable between zero and 20° so that for large positive and negative slopes of the object's surface, a beveled edge (360) can be used to follow the calculated surface line (362). Note that by placing the focus (364) at or slightly above the exposed surface of a lamination, a cut such as shown by cut (366) with a negative slope, can be performed. If the focus (364) is positioned midway through a lamination, a cut can be varied from positive to negative slopes in the same lamination. Such laser beams (348) make LOM processes possible with relatively thick laminations (358), which reduces the time required to make a particular object.

Figure 54:
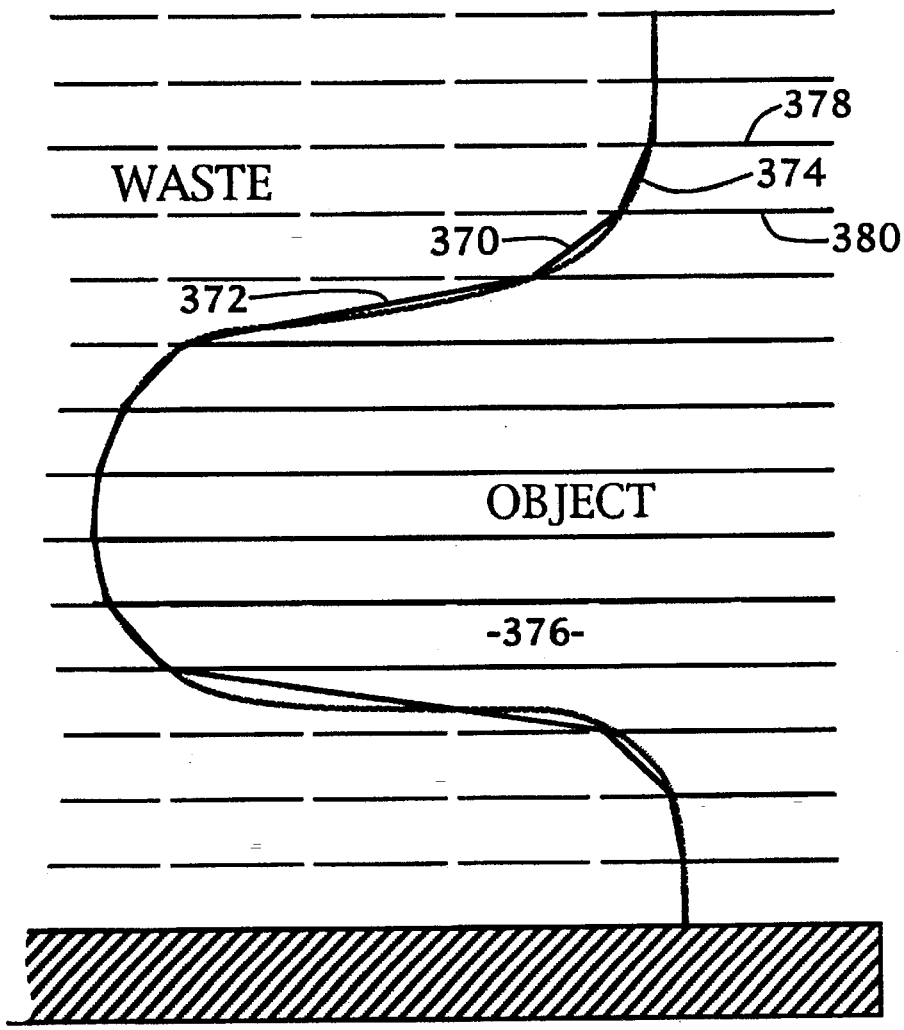
FIG. 54 is an elevational cross-sectional view of a stack similar to those shown in FIGS. 50 and 51 as cut by a laser beam controllable over five axes, wherein the laser cuts are made between the upper and lower surface intersections of the calculated surface of the object.
Figure 55:
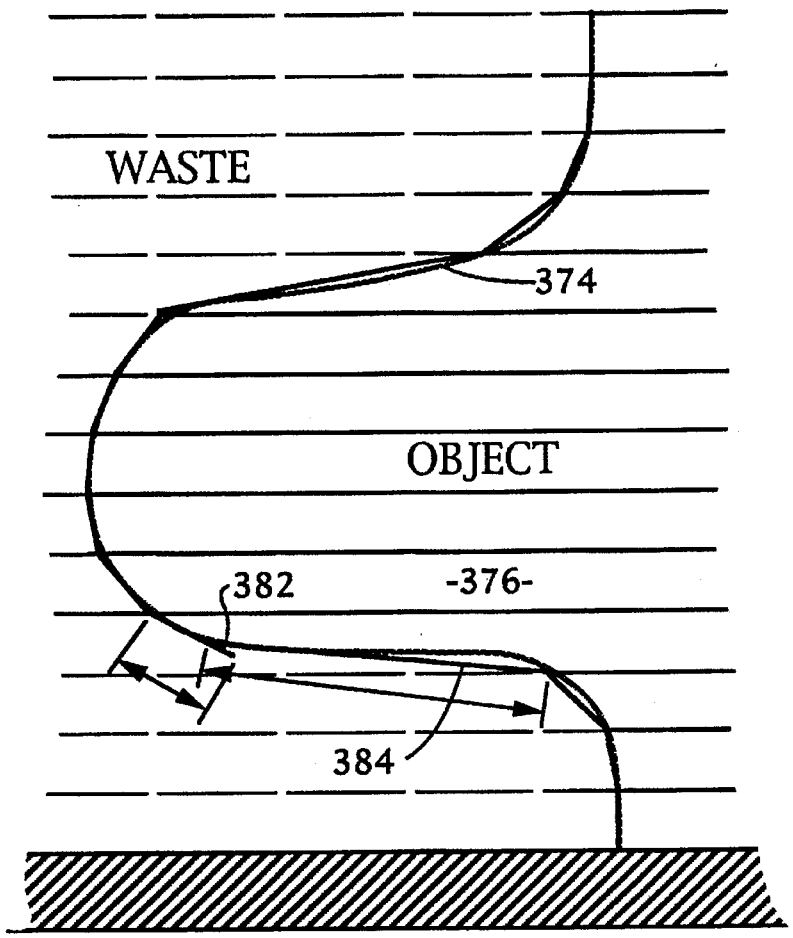
FIG. 55 is an elevational cross-sectional view similar to FIG. 54 showing that the cuts may also be made on chords to assure the object is fully present, and that for long cuts on a lamination, a slice edge may be formed with multiple cuts.

FIGS. 54 and 55 show cuts (370) made by a laser beam supported for movement on a five axis manipulator, so that the cuts (370) can be beveled to closely approximate the calculated edge surface (374) of the object (376). Note that cut (372) is substantially longer that cut (370), which requires either a more intense cutting beam or the slowing down thereof to make such a deep cut (372). The cuts as shown in FIG. 54 are between the intersections of the surface line (374) and the top and bottom surfaces (378) and (380) of the laminations. As shown in FIG. 55, the cuts can be calculated to stay outside of the surface line (374) of the object (376) and for extreme angles, two cuts (382) and (384) can be used at undercut areas to avoid leaving too much material.

Figures 56, 57:
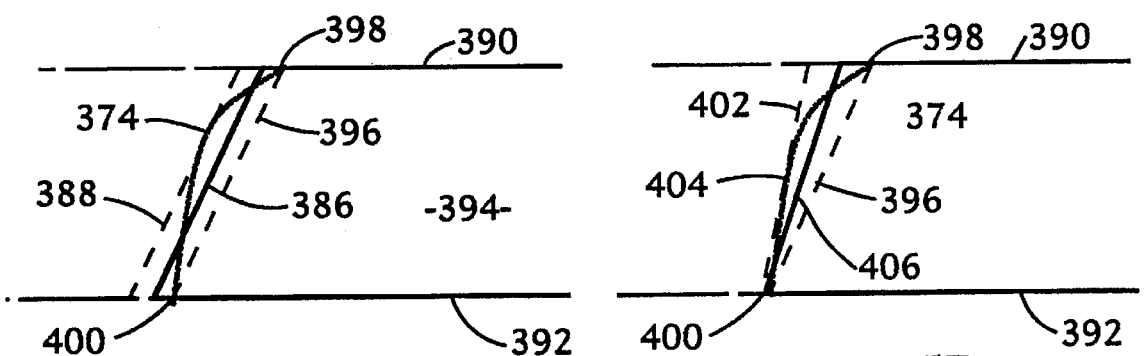
FIG. 56 is a highly enlarged, elevational cross-sectional view showing one method of cutting a bevel edge on a slice when substantial curvature is present, the cut being made midway between a line extending between the intersections of the calculated object surface with the upper and lower surfaces of the slice and a parallel outer chord line.
FIG. 57 is a view similar to FIG. 56 showing another method where the cut is made midway between a line extending between the intersections of the calculated object surface with the upper and lower surfaces of the slice and a chord on the calculated object's surface taken at a mid-point in the slice.

When the curvature of the surface line (374) changes slope substantially during a lamination as shown in FIGS. 56 and 57, various compromise methods can be used to determine the proper cut line (386). As shown in FIG. 56, they include cutting on the outermost chord (388) parallel to a line drawn between the intersections of the surface line (374) and the upper and lower surfaces (390) and (392) of a slice (394), at the line (396) extending between the intersections (398) and (400) of the surface line (374) and the upper and lower surfaces (390) and (392) of the slice (394), or at a parallel midpoint cut (386) therebetween. It is also possible (FIG. 57) to calculate a chord line (402) from a midpoint (404) between the upper and lower surfaces (390) and (392) on the surface line (374) for the cut line or a compromise cut line (406) positioned between the lines (396) and (402).

Figure 58:
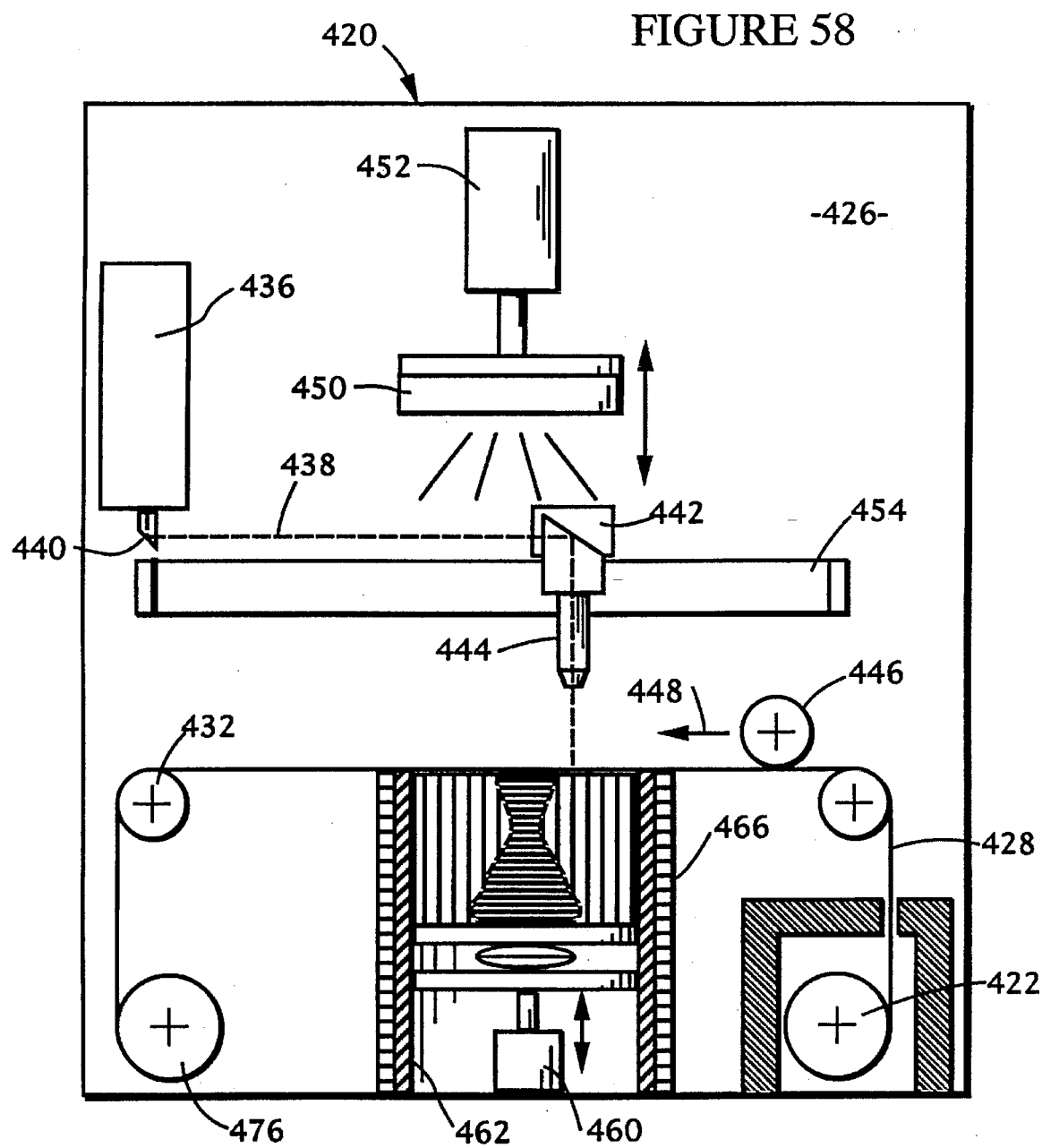
FIG. 58 is a diagrammatic view of a LOM with temperature controls for the stack.

An environmentally controlled LOM (420) is shown in FIG. 58, it having a supply roll (422) retained within a refrigerating cabinet (424) since the interior (426) of the machine (420) is held at an elevated temperature.

The machine (420) feeds a ribbon (428) over two rollers (430) and (432) which maintain the height of the ribbon (428) in the proper location to be added to the stack (434). With a fresh section of ribbon (428) in place, a laser (436) produces a beam (438) reflected by mirrors (440) and (442) to a prism lens system (444), which directs the beam (438) onto the ribbon (428) adjacent to the stack (434) once the ribbon (428) has been bonded to the stack (434) by the hot roller (446), which moves there across in the directions of arrow (448). In addition to the hot roller (446), a UV lamp (450) may be positioned above the stack (434) to assist in the bonding process. The lamp (450) may be mounted on a plunger (452) so it can be moved down towards the stack (434) for efficiency and then lifted for clearance of the XY positioner (454) which moves the lens system (444) to the proper locations to form an object (456). Instead of a UV lamp (450), the plunger (452) can have a compression plate (not shown) thereon for directly applying pressure between the ribbon (428) and the stack (434).

The stack (434) is elevated by a jack (460) within a support cylinder (462). The jack (460) maintains the upper surface (464) of the stack (434) in proper position for attachment to the ribbon (428) and for cutting by the laser beam (438). The cylinder (462) helps support the stack (434) which moves up and down therein. The cylinder (462) is maintained at a constant elevated temperature by a heated jacket (466) thereabout. Preferably the heated jacket (466) maintains the stack (434) just below its bonding temperature so that thermal stresses within the stack (434) otherwise caused by heat bonding are minimized.

Figure 59:
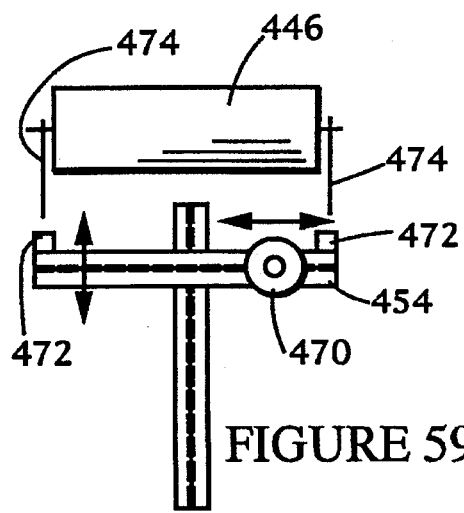
FIG. 59 is a diagrammatic view showing how the XY positioner of FIG. 58 in addition to moving the laser can be used to move the hot or compressing roller.

As shown in FIG. 59, the XY positioner (454) can have a laser (470) mounted directly thereto. This eliminates the need for precision alignment of mirrors. However, such configuration is only possible when small lightweight high power lasers (470) are available and generally the XY positioner (454) must be robust to be able to quickly move the increased mass of the laser (470). A robust XY positioner (454) can used to drive the roller (446) by providing releasable locks (472) thereon, which engage hooks (474) connected with the roller (446). When the XY positioner (454) is used to move both the laser (470) and the compressing roller (446), the expense of a another drive means is avoided.

Figure 60:
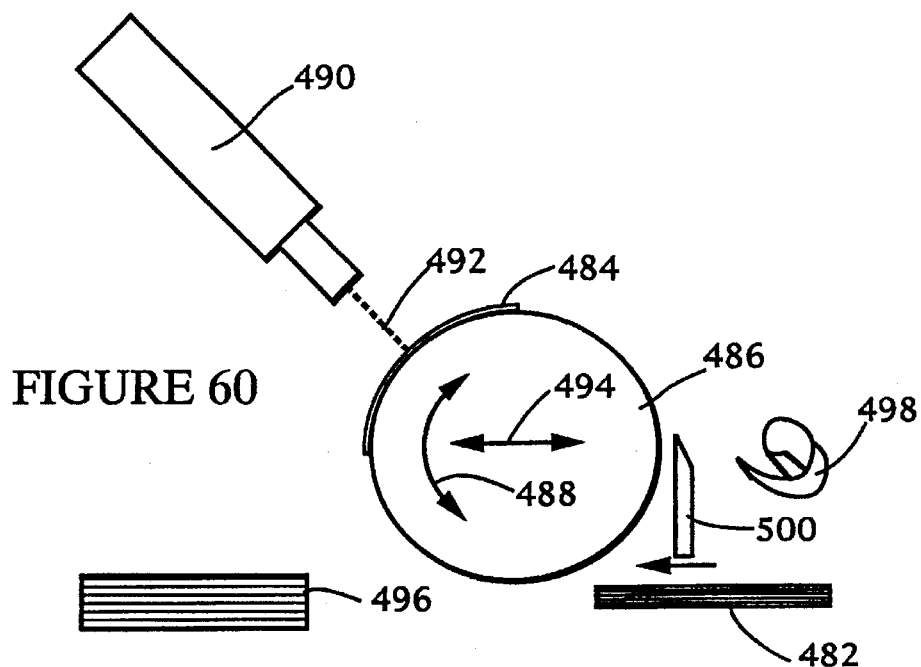
FIG. 60 is a diagrammatic view of an LOM where sheets are picked up electrostatically, magnetically or with vacuum onto the roller for cutting with a laser and then positioning on a stack.
Figure 61:
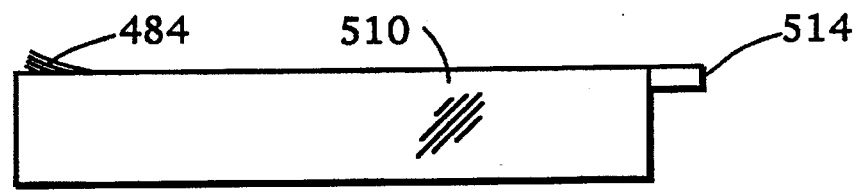
FIG. 61 is a side view of a sheet feeder module having indica thereon so that the type of sheet therein can be determined by the LOM.
Figure 62:
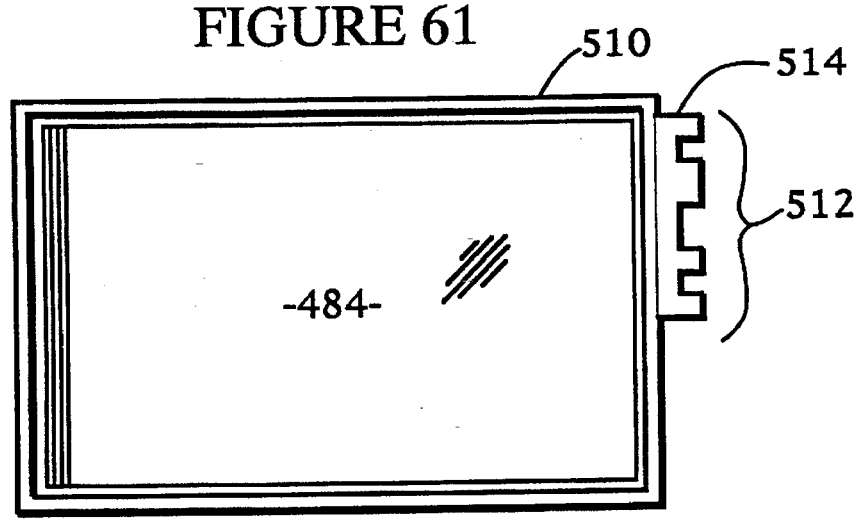
FIG. 62 is a top plan view of the sheet feeder module of FIG. 61.

Instead of the ribbon feed to a waste roller (476) as shown in FIG. 58, the LOM (480) of FIG. 60 includes a sheet feeder (482) with individual sheets (484) being picked up by a roller (486) by means such as vacuum, magnetism or electrostatics. The roller (486) rotates in the directions of arrow (488) so that the laser (490) only needs to be translated longitudinally along the roller (486) for its laser beam (492) to cut the proper object slices. Once the sheet (484) has been cut, the roller (486) is translated horizontally in the directions of arrow (494) and at the same time rotated so that the sheet (484) is properly position on the stack (496). The entire sheet (484) can be left on the stack (496) or when the sheet (484) is selectively bonded to the stack (496), the waste (498) can be retained on the roller (486) for later removal by the doctor knife (500). A typical container (510) for sheets (484) is shown in FIG. 61 and 62. Sheet feeding mechanisms such as are used in laser printers and reproduction machines are suitable to get a sheet (484) to the roller (486). Note that the container (510) include sheet indica (512) on an extension (514) thereof. Although mechanical keys are shown, bar codes, magnetic strips or other suitable readable indica can be used to indicate the type of sheets (484) contained within the container (510). The information conveyed could be size, thickness, type of sheet, type or existence of adhesive, color, or almost any other physical characteristic of the sheets (484).

Figure 63:
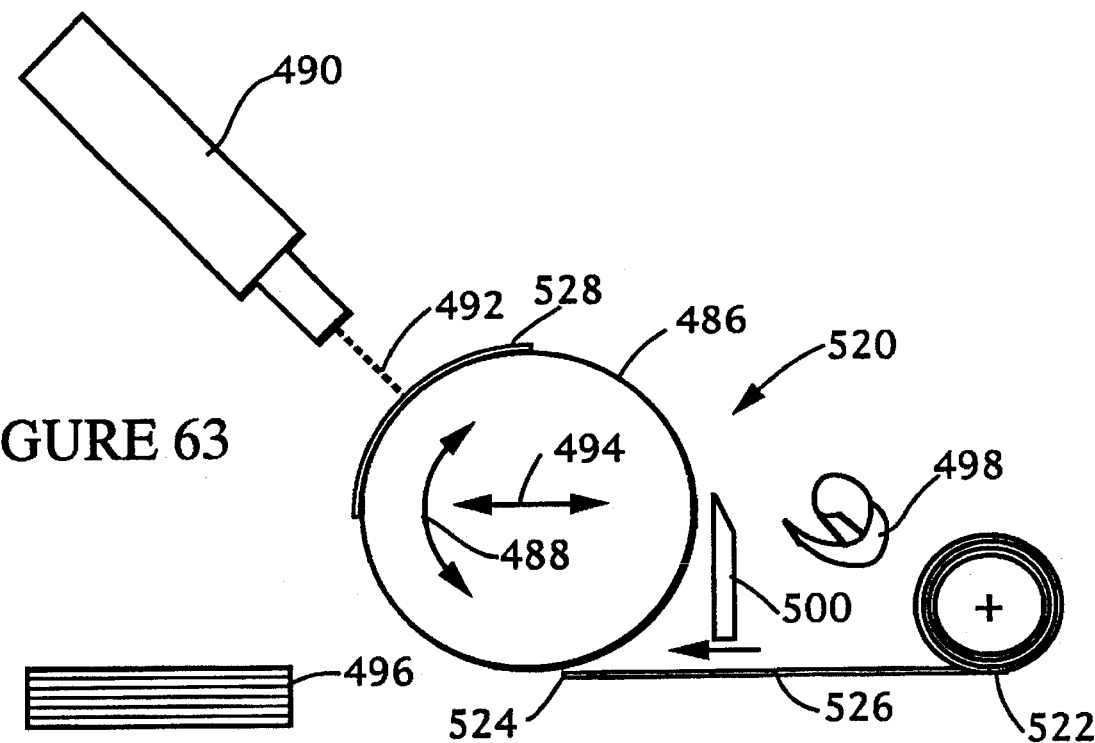
FIG. 63 is a diagrammatic view similar to FIG. 60 only instead having lamination stock fed by a ribbon.

A modified LOB (520) similar to LOM (480) is shown in FIG. 63, it having a roll feeder (522) instead of a sheet feeder. Generally it operates by feeding the end (524) of the ribbon (526) up on the roller (486). Thereafter, a piece (528) is cut from the ribbon (526) by the laser (490) and the ribbon (526) is retracted to the position shown. Thereafter, the LOM (520) operates like LOM (480) to cut laminations and place them on the stack (496).

Figure 64:
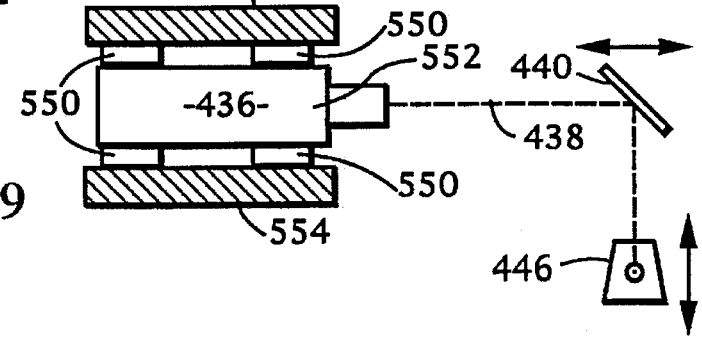
FIG. 64 is diagrammatic view of laser mounting for the LOM of FIG. 58 so that lasers can be aligned at the factory and thereafter be interchanged.

Occasionally lasers fail in the field and must be replaced. No matter want type laser mounting is used, alignment of the laser can be a difficult maintenance problem since laser manufacturers do not precisely align the lasers with their cases. Referring to FIG. 64, the laser (436) has had its laser beam (438) precisely aligned with respect to mounting blocks (550) in a factory optical facility. The blocks (550) are aligned with the beam (438) no matter what the alignment of the case (552) of the laser (436) might have been. By providing precise mounting plates (554 and 556) on the LOM for the blocks (550), the beam (438) remains properly aligned even when the laser (436) is changed during field maintenance.

Figure 65:
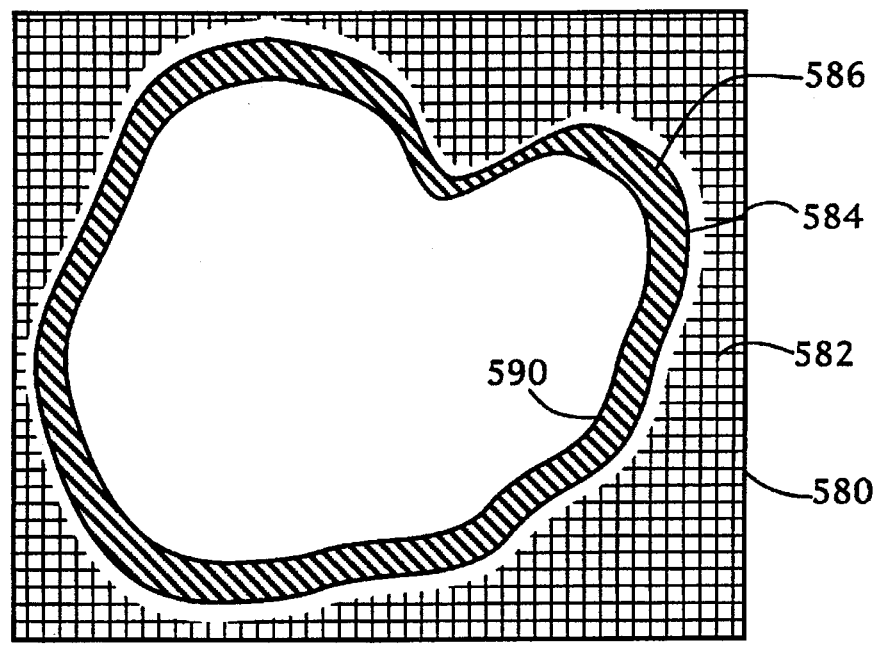
FIG. 65 is a top plan view through an object form which has been metalized so that it can be used to mold the object.

Although heretofore, the invention has primarily been concerned about directly forming objects, as shown in FIG. 65, it also can be used to construct molds for objects. FIG. 65 is a top elevational view of one (580) of a plurality of laminations in which the cross hatching (582) for release does not extend quite to the inner surface (584). The inner surface (584) has a metal layer (586) applied thereto, whose width has been exaggerated for clarity. The metal layer (586) forms a shell through the plurality of laminations (580). Once formed, whether it continues to be supported by the laminations cross-hatching (582), it provides a mold surface (590) into which plastic or other curable material can be poured to form the final object.

Thus there has been shown and described novel processes, methods, objects and apparatus to perform and produce the same which fulfill all of the objects and advantages sought therefor. Many changes, alterations, modifications and other uses and applications of the subject laminated, solid modeling technique will become apparent to those skilled in the art after considering this specification together with the accompanying drawings. All such changes, alterations and modifications that do not depart from the spirit and scope of the invention are deemed to be covered by the invention, which is limited only by the claims which follow.

We claim:

1. A method of converting sheet material into a three-dimensional object comprised of a plurality of slices, including the steps of:

positioning a layer of said sheet material over a work station;

bonding said layer to an adjacent layer of sheet material to result in a bonded layer using a bonding tool movably mounted over the work station;

forming a slice in said layer using a forming tool movably mounted over the work station, portions of said layer not defining part of said slice being unwanted; and forming lines in said unwanted portions with said forming tool to facilitate removal of said unwanted portions after said three-dimensional object is formed, said lines in said unwanted portions closer to the edges of said slice being spaced closer together than the lines farther from the edges of said slice.

2. The method of claim 1, wherein said step of forming said lines in said unwanted portions comprises forming a cross-hatched pattern in said unwanted portions with at least some of said lines intersecting.

3. The method of claim 2, wherein said step of forming the cross-hatched pattern comprises forming the pattern to be more dense closer to the edges of said slice than the cross-hatched pattern farther from the edges of said slice.

4. The method of claim 2, wherein said step of forming said slice comprises defining an inner edge of said slice surrounding an interior unwanted portion and defining an outer edge of said slice surrounded by an exterior unwanted portion.

5. The method of claim 4, wherein said step of forming said cross-hatched pattern comprises forming said pattern in both said interior and exterior unwanted portions.

6. The method of claim 4, wherein said step of forming said cross-hatched pattern comprises forming said pattern in only said exterior unwanted portion, and the method further comprises removing said interior unwanted portion prior to positioning a subsequent layer of said sheet material over the work station.

7. The method of claim 6, wherein said forming tool is a laser and said step of removing said interior unwanted portion comprises burning away said interior unwanted portion with said laser.

8. A method of converting layers of material into a three-dimensional object comprised of a plurality of slices of said material, including the steps of:

positioning a layer of said sheet material over a work station on which a plurality of layers have been previously positioned and bonded together to form a stack;

bonding said layer to said stack;

defining edges of a slice in said layer bonded to said stack using a forming tool movably mounted over the work station, portions of said layer not defining part of said slice being unwanted; and heating only said unwanted portions of said layer sufficiently to weaken the bonds between the unwanted portions and an adjacent layer in said stack to facilitate removal of said unwanted portions after said three-dimensional object is formed.

9. The method of claim 8, further including the step of:

forming a cross-hatched pattern in said unwanted portions with said forming tool so that at least some of said lines intersect other lines in said unwanted portions to facilitate removal of said unwanted portions after said three-dimensional object is formed.

10. The method of claim 8, wherein said step of heating is performed by said forming tool which applies energy to said layer.

11. The method of claim 10, wherein said step of bonding is performed by a forming tool which applies energy to activate heat-sensitive adhesive on said layer to bond it to said stack.

12. The method of claim 10, wherein said step of bonding is performed by a bonding tool which moves relative to said work station and applies force to said stack to bond adjacent layers of material to each other.

13. A method of converting layers of material into a three-dimensional object comprised of a plurality of slices of said material, including the steps of:

positioning a layer of said sheet material over a work station on which a plurality of layers have been previously positioned and bonded together to form a stack;

bonding said layer to said stack;

defining edges of a slice in said layer bonded to said stack using a forming tool movably mounted over the work station, portions of said layer not defining part of said slice being unwanted; and burning said unwanted portions to form an indentation and prevent unwanted portions in subsequent layers from bonding to said stack.

14. The method of claim 13, wherein said step of burning is performed by said forming tool which applies energy to said layer.

15. The method of claim 14, wherein said step of bonding is performed by said forming tool which applies energy to activate heat-sensitive adhesive on said layer to bond it to said stack.

16. The method of claim 14, wherein said step of bonding is performed by a bonding tool which moves relative to said work stage and applies force to bond adjacent layers of material to each other.

17. A method of converting layers of sheet material into a three-dimensional object comprised of a plurality of slices of said material, including the steps of:

defining a slice in a layer of said sheet material;

positioning said layer of said sheet material over a work station on which a plurality of layers have been previously positioned and bonded together to form a stack;

weakly bonding said layer to said stack;

strongly bonding regions of said layer of said sheet material forming said slice to said stack using a forming tool movably mounted over said work station, without strongly bonding portions of said layer not defining part of said slice to said stack to facilitate removal of said portions; and disconnecting said slice from said layer using said forming tool.

18. The method of claim 17, wherein said step of weakly bonding is performed by a roller which moves relative to said work stage and applies force to bond adjacent layers of material to each other.

19. The method of claim 18, wherein said step of strongly bonding is performed by said forming tool which applies energy to said layer.

20. The method of claim 19, wherein said step of disconnecting is performed by said forming tool which applies focussed energy to said layer.

21. A laminated object manufacturing system for forming material into a three-dimensional object comprised of a plurality of layers of said material, comprising:

a handling mechanism for supplying the material to a work stage, the work stage adapted to position said material;

a forming tool mounted to move relative to said work stage to form said layers from the material;

a bonding tool mounted to move relative to said work stage to apply force and bond adjacent layers of material to each other, a sensor mounted to sense the force applied by said bonding tool to the material during bonding of said adjacent layers; and a controller which regulates the relative position of said bonding tool and said work stage in accordance with the force sensed by said sensor.

22. The system of claim 21, wherein said work stage defines a work surface, and said bonding tool is a roller mounted to move across said surface.

23. The system of claim 22, wherein said work surface is generally flat, and said one of said roller and said work stage is movable with respect to the other so as to displace said roller in a first direction parallel to said work surface.

24. The system of claim 23, wherein said work stage is positionable in a second direction generally perpendicular to said work surface, wherein said controller regulates the relative positions of said roller and said work stage in the second direction thereby regulating said bonding force therebetween.

25. The system of claim 22, wherein said material is a sheet pre-coated with adhesive.

26. The system of claim 25, wherein said material is a sheet pre-coated with heat-sensitive adhesive and said roller is heated.

27. The system of claim 21, wherein said material is a sheet and said handling mechanism comprises a supply roller and a receiving roller disposed on opposite sides of said work stage and adapted to deliver said sheet across said work stage.

28. The system of claim 21, wherein said material is powder and said handling mechanism comprises a container for said powder and a movable carriage supporting said work stage and adapted to position said work stage under said container.

29. The system of claim 21, wherein said forming tool is a laser mounted above said work stage to apply a laser beam to said material to form said layers.

30. A laminated object manufacturing system for forming material into a three-dimensional object comprised of a stack of slices of the material, comprising:

a work stage adapted to position said stack;

a handling mechanism for supplying incremental layers of material to the work stage;

a forming tool mounted to move relative to said work stage to shape said slices from said incremental layers of material;

a sensor mounted to sense the height of said stack on said work stage; and a controller which receives input from said sensor and divides the height of the stack by the number of layers previously placed on said stack to obtain an average layer height and predict the height of the next layer, and outputs information to said forming tool regarding the shape of the next slice based on the stack height and a predicted next layer height.

31. The system of claim 30, wherein said material is a sheet and said handling mechanism comprises a supply roller and a receiving roller disposed on opposite sides of said work stage and adapted to deliver said sheet across said work stage, and said forming tool is a laser mounted above said work stage to apply a laser beam to said sheet to form said slices.

32. The system of claim 30, including a bonding tool mounted to move relative to said work stage to apply force and bond adjacent layers of material to each other.

33. The system of claim 32, wherein said sensor is a force sensor mounted to support said bonding tool so as to sense a load between said bonding tool and said stack, said controller receiving said load and calculating the stack height therefrom.

34. The system of claim 32, wherein said work stage is adapted to position said stack relative to said bonding tool and said controller is connected to adjust the relative height between said stack and said bonding tool to ensure proper bonding based on the stack height measurement.

35. The system of claim 32, wherein said bonding tool and said sensor are mounted on a common frame.

* * * * *